United States Patent
Cheng

(10) Patent No.: US 12,135,388 B2
(45) Date of Patent: Nov. 5, 2024

(54) FMCW RADAR, METHOD FOR PROCESSING DIGITAL SIGNALS, AND CHARACTERIZATION INFORMATION DETECTION METHOD

(71) Applicant: Wistron Corporation, New Taipei (TW)

(72) Inventor: Kai-Jen Cheng, New Taipei (TW)

(73) Assignee: WISTRON CORPORATION, New Taipei (TW)

( * ) Notice: Subject to any disclaimer, the term of this patent is extended or adjusted under 35 U.S.C. 154(b) by 463 days.

(21) Appl. No.: 17/349,264

(22) Filed: Jun. 16, 2021

(65) Prior Publication Data
US 2022/0299598 A1 Sep. 22, 2022

(30) Foreign Application Priority Data
Mar. 17, 2021 (TW) ................. 110109640

(51) Int. Cl.
*G01S 7/35* (2006.01)
*A61B 5/05* (2021.01)
*G01S 7/41* (2006.01)

(52) U.S. Cl.
CPC ............ *G01S 7/354* (2013.01); *G01S 7/415* (2013.01); *A61B 5/05* (2013.01); *G01S 7/356* (2021.05)

(58) Field of Classification Search
CPC ........ G01S 13/88; G01S 13/50; G01S 13/524; G01S 7/40; G01S 7/4056; G01S 7/415; G01S 7/356; G01S 7/354
USPC .................. 342/173, 192, 28, 195; 375/346; 455/296
See application file for complete search history.

(56) References Cited

U.S. PATENT DOCUMENTS

| 3,877,010 | A | * | 4/1975 | Holberg | G01S 13/5244 342/162 |
| 4,431,995 | A | * | 2/1984 | Barton | G01S 3/42 342/373 |
| 5,390,133 | A | * | 2/1995 | Sohie | G06V 10/255 342/159 |
| 6,603,424 | B1 | * | 8/2003 | Abatzoglou | G01S 13/904 342/25 R |

(Continued)

FOREIGN PATENT DOCUMENTS

| CN | 111060903 A | 4/2020 |
| CN | 111142102 A | 5/2020 |

(Continued)

OTHER PUBLICATIONS

Examination report dated Jan. 25, 2022, listed in related European patent application No. 21 190 065.9.

(Continued)

*Primary Examiner* — Ladimir Magloire
*Assistant Examiner* — Michael W Justice
(74) *Attorney, Agent, or Firm* — McClure, Qualey & Rodack, LLP

(57) ABSTRACT

A method for processing digital signals is provided. In the method, a plurality of digital signals corresponding to radar signals received by a receiving terminal are superposed, so as to reduce noise caused by environmental interference. Therefore, according to an output signal obtained after the superposition, accurate characterization information of a to-be-detected object can be obtained.

23 Claims, 23 Drawing Sheets

(56) References Cited

U.S. PATENT DOCUMENTS

| | | | | |
|---|---|---|---|---|
| 6,809,681 B1* | 10/2004 | Niechayev | ............ | G01S 13/582 342/159 |
| 6,822,606 B2* | 11/2004 | Ponsford | ................ | G01S 3/74 342/159 |
| 7,477,758 B2* | 1/2009 | Piirainen | ........... | B60R 21/01516 701/44 |
| 7,623,222 B2* | 11/2009 | Benz | ................ | G01S 17/10 356/5.1 |
| 7,773,031 B2* | 8/2010 | Gazelle | ................ | G01S 7/2926 342/174 |
| 8,717,230 B1* | 5/2014 | Fischi | ................ | G01S 13/5244 342/194 |
| 8,742,935 B2* | 6/2014 | Cuddihy | ............ | G08B 21/0469 340/573.7 |
| 10,037,671 B2* | 7/2018 | Zack | ................ | G08B 25/016 |
| 10,227,054 B2 | 3/2019 | Diewald | | |
| 10,514,770 B2* | 12/2019 | Malysa | ................ | G01S 13/584 |
| 10,969,463 B2* | 4/2021 | Melzer | ................ | G01S 13/584 |
| 11,054,913 B2* | 7/2021 | Malysa | ................ | G01S 13/34 |
| 11,125,866 B2* | 9/2021 | Sumi | ................ | G01S 7/52023 |
| 11,204,647 B2* | 12/2021 | Rao | ................ | G01S 7/41 |
| 11,378,648 B2* | 7/2022 | Xie | ................ | A61B 5/05 |
| 11,385,344 B2* | 7/2022 | Peng | ................ | G01S 7/354 |
| 11,415,670 B2* | 8/2022 | Tyagi | ................ | G01S 7/415 |
| 11,774,553 B2* | 10/2023 | Santra | ................ | G01S 7/417 342/109 |
| 2004/0178951 A1* | 9/2004 | Ponsford | ................ | G01S 7/32 342/194 |
| 2006/0251293 A1* | 11/2006 | Piirainen | ........... | B60R 21/01552 382/104 |
| 2007/0013580 A1* | 1/2007 | Finch | ................ | G01S 13/5246 342/194 |
| 2008/0304043 A1* | 12/2008 | Benz | ................ | G01S 7/4865 356/5.01 |
| 2009/0201195 A1* | 8/2009 | Gazelle | ............... | G01S 13/0209 342/174 |
| 2010/0152600 A1* | 6/2010 | Droitcour | ............ | A61B 5/1113 600/534 |
| 2012/0106609 A1* | 5/2012 | Kim | ................ | H04L 25/0222 375/346 |
| 2013/0002434 A1* | 1/2013 | Cuddihy | ................ | G01S 13/18 342/28 |
| 2016/0379462 A1* | 12/2016 | Zack | ................ | G08B 25/016 340/539.12 |
| 2017/0074974 A1 | 3/2017 | Rao et al. | | |
| 2017/0364160 A1* | 12/2017 | Malysa | ................ | G01S 7/415 |
| 2018/0279884 A1 | 10/2018 | Ahmad et al. | | |
| 2019/0087009 A1* | 3/2019 | Rao | ................ | G01S 7/352 |
| 2019/0113600 A1* | 4/2019 | Melzer | ................ | G01S 13/931 |
| 2019/0129026 A1* | 5/2019 | Sumi | ................ | G01S 7/52033 |
| 2019/0391251 A1 | 12/2019 | Bharadwaj, Jr. et al. | | |
| 2020/0064444 A1* | 2/2020 | Regani | ................ | G01S 7/417 |
| 2020/0081110 A1 | 3/2020 | Nam et al. | | |
| 2020/0116850 A1 | 4/2020 | Santra et al. | | |
| 2020/0125180 A1* | 4/2020 | Malysa | ................ | G06F 3/01 |
| 2020/0264273 A1* | 8/2020 | Xie | ................ | A61B 5/024 |
| 2020/0268257 A1 | 8/2020 | Wu et al. | | |
| 2020/0386879 A1* | 12/2020 | Shouldice | ................ | G01S 13/88 |
| 2021/0072346 A1 | 3/2021 | Bogner et al. | | |
| 2021/0293927 A1* | 9/2021 | Tyagi | ................ | G01S 13/723 |
| 2021/0293948 A1* | 9/2021 | Peng | ................ | G01S 7/415 |
| 2021/0389439 A1* | 12/2021 | Sumi | ................ | G01S 7/52025 |
| 2021/0396843 A1* | 12/2021 | Santra | ................ | G01S 7/415 |
| 2022/0299624 A1* | 9/2022 | Peng | ................ | G01S 13/345 |

FOREIGN PATENT DOCUMENTS

| | | |
|---|---|---|
| CN | 111295596 A | 6/2020 |
| EP | 3425419 A1 | 1/2019 |
| WO | 2019113517 A1 | 6/2019 |
| WO | 2020/226638 A1 | 11/2020 |

OTHER PUBLICATIONS

Ahmad, A., et al.; "Vital Signs Monitoring of Multiple People using a FMCW Millimeter-Wave Sensor," IEEE; 2018; pp. 1450-1455.

* cited by examiner

FMCW RADAR, METHOD FOR PROCESSING DIGITAL SIGNALS, AND CHARACTERIZATION INFORMATION DETECTION METHOD

CROSS-REFERENCE TO RELATED APPLICATION

This non-provisional application claims priority under 35 U.S.C. § 119(a) to Patent Application No. 110109640 filed in Taiwan, R.O.C. on Mar. 17, 2021, the entire contents of which are hereby incorporated by reference.

BACKGROUND

Technical Field

The present invention relates to radar signal processing technologies, and in particular, to a frequency modulated continuous wave (FMCW) radar, a method for processing digital signals, and a characterization information detection method.

Related Art

A radar technology can be applied to a large number of outdoor fields such as speed measurement and ranging. However, in an indoor field, a large number of environmental interference factors cause inaccurate measurement results. For example, floors, walls, and cabinets cause signal reflection interference, and object movements such as swaying of a curtain and fan rotation can also cause signal disturbance.

SUMMARY

In view of this, according to some embodiments, the FMCW radar includes a transmitter and a receiver. The transmitter is configured to transmit a plurality of chirp signals. The receiver is configured to receive reflected chirp signals and generate a plurality of digital signals corresponding to the chirp signals. The receiver then superposes the digital signals to obtain an output signal, and calculates characterization information of a to-be-detected object according to the output signal.

According to some embodiments, the receiver superposes the digital signals corresponding to the chirp signals in the same frame to obtain the output signal.

According to some embodiments, the receiver superposes the digital signals corresponding to the chirp signals in a plurality of adjacent frames to obtain the output signal.

According to some embodiments, the receiver aligns the digital signals before superposing the digital signals.

According to some embodiments, the transmitter includes at least one transmitting antenna. The receiver superposes the digital signals corresponding to the chirp signals from the same transmitting antenna.

According to some embodiments, the receiver includes a plurality of receiving antennas. The receiver superposes the digital signals corresponding to the chirp signals from the same transmitting antenna received by one of the receiving antennas to obtain an output signal.

According to some embodiments, the receiver includes a plurality of receiving antennas. The receiver superposes the digital signals corresponding to the chirp signals from the same transmitting antenna received by the receiving antennas to obtain an output signal.

According to some embodiments, the transmitter includes a plurality of transmitting antennas. The receiver superposes the digital signals corresponding to the chirp signals from at least two of the transmitting antennas.

According to some embodiments, the receiver includes a plurality of receiving antennas. The receiver superposes the digital signals corresponding to the chirp signals from at least two of the transmitting antennas received by one of the receiving antennas to obtain an output signal.

According to some embodiments, the receiver includes a plurality of receiving antennas. The receiver superposes the digital signals corresponding to the chirp signals from at least two of the transmitting antennas received by the receiving antennas to obtain an output signal.

According to some embodiments, the receiver further generates statistical information according to the output signal and corrects the output signal according to the statistical information.

According to some embodiments, the statistical information is an absolute sum of squares, an absolute maximum, a standard deviation, or a variance.

According to some embodiments, the receiver determines, according to the output signal and a machine learning model, whether the to-be-detected object is present in a detection area.

According to some embodiments, when determining that the to-be-detected object is present, the receiver calculates the characterization information of the to-be-detected object according to the output signal.

According to some embodiments, a method for processing digital signals is performed by a processor in a signal processing device and includes: superposing a plurality of digital signals corresponding to a plurality of chirp signals received by a receiving terminal of a Doppler radar to obtain an output signal; and calculating characterization information of the to-be-detected object according to the output signal.

According to some embodiments, the digital signals corresponding to the superposed chirp signals are located in the same frame or in a plurality of adjacent frames.

According to some embodiments, the to-be-superposed digital signals are aligned before the digital signals are superposed.

According to some embodiments, the method for processing digital signals further includes: generating statistical information according to the output signal; and correcting the output signal according to the statistical information.

According to some embodiments, the method for processing digital signals further includes: determining, according to the output signal and a machine learning model, whether the to-be-detected object is present in a detection area.

According to some embodiments, the step of calculating characterization information of the to-be-detected object according to the output signal is performed when it is determined that the to-be-detected object is present.

According to some embodiments, the characterization information detection method includes: receiving a plurality of digital detection signals corresponding to a Doppler radar; performing a frequency domain analysis on the digital detection signals to obtain a plurality of frequency domain detection signals; generating statistical information according to the frequency domain detection signals; correcting the frequency domain detection signals according to the statistical information; determining, according to the corrected frequency domain detection signals and a machine learning model, whether the to-be-detected object is present in a detection area; and calculating characterization information of the to-be-detected object according to the corrected frequency domain detection signals in response to the to-be-detected object being present.

Based on the above, according to the FMCW radar, the method for processing digital signals, and the characterization information detection method in some embodiments, the problem of poor signals caused by interference from static and dynamic environments can be solved, and an amount of to-be-processed data can be reduced to accelerate a processing speed. According to the FMCW radar, the method for processing digital signals, and the characterization information detection method in some embodiments, it can be identified whether the to-be-detected object is present, so as to improve processing efficiency and filter erroneous determination.

DETAILED DESCRIPTION

Figure 1:
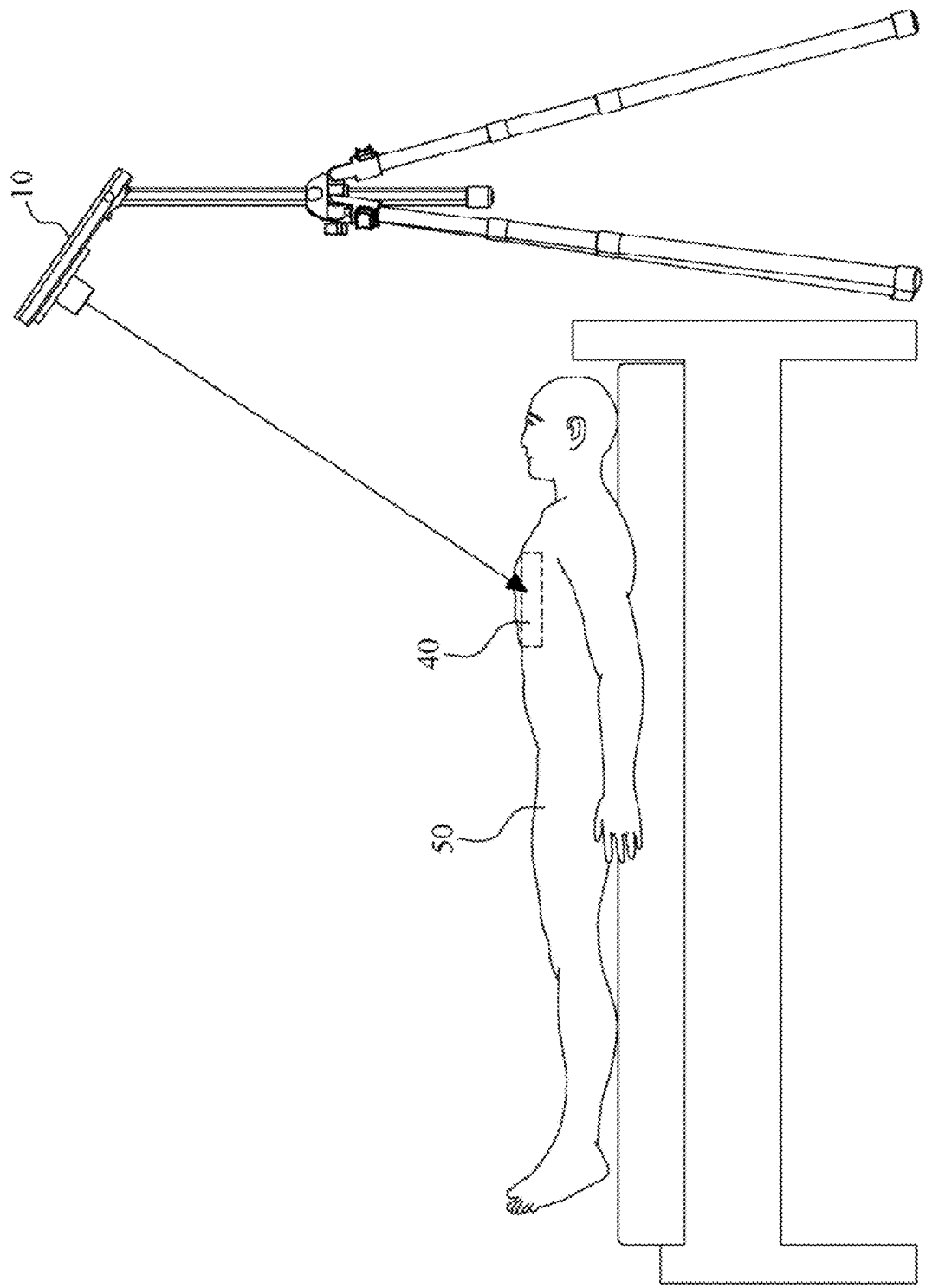
FIG. 1 is a schematic diagram of a usage status of an FMCW radar according to some embodiments.

FIG. 1 is a schematic diagram of a usage status of an FMCW radar 10 according to some embodiments. The FMCW radar 10 can detect a detection area 40. A detection result may be used to calculate one or more information of a to-be-detected object 50, for example, a distance, a direction, a moving speed, physiological information (such as heartbeats, breathing), and the like. The to-be-detected object 50 may be, for example, but not limited to a biological body (such as a human body).

Figure 2:
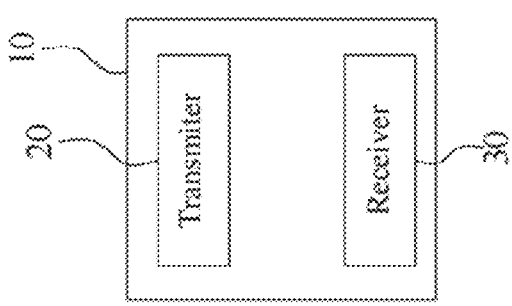
FIG. 2 is a schematic block diagram of the FMCW radar according to some embodiments.

FIG. 2 is a schematic block diagram of the FMCW radar 10 according to some embodiments. The FMCW radar 10 includes a transmitter 20 and a receiver 30. The transmitter 20 transmits a radar signal, and the receiver 30 receives a reflected radar signal.

Figure 3:
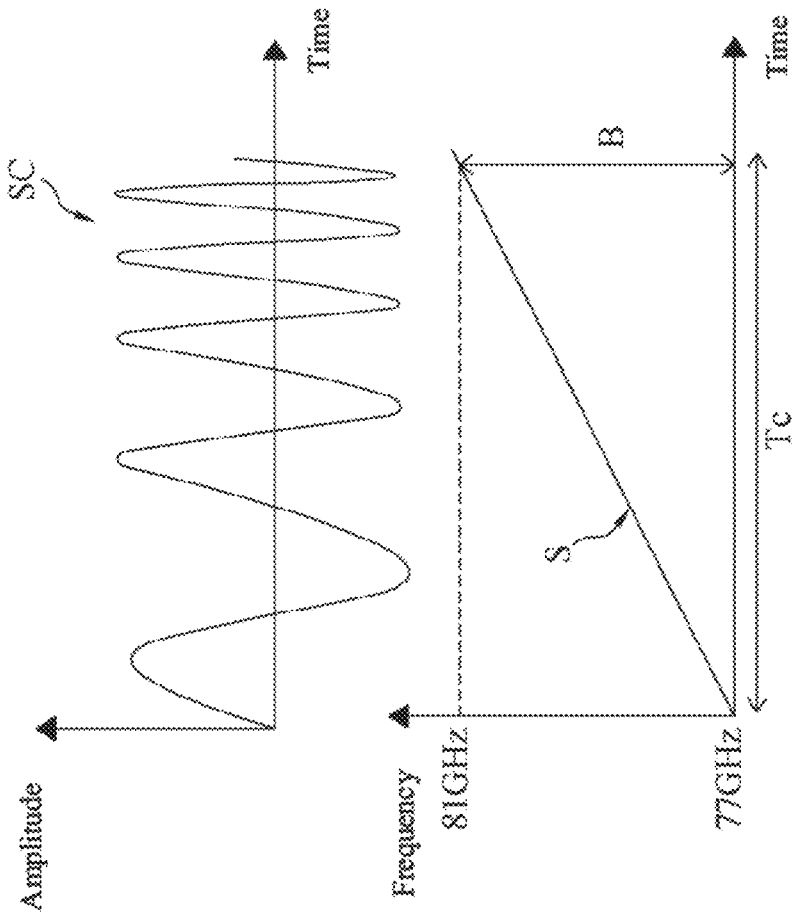
FIG. 3 is a schematic diagram illustrating a radar signal.

Referring to FIG. 3, FIG. 3 is a schematic diagram illustrating the radar signal. The upper half shows a change in an amplitude of the radar signal with time, and the lower half shows a change in a frequency of the radar signal with time. The radar signal transmitted by the transmitter 20 includes a plurality of chirp signals SC. For clarity of the drawing, FIG. 3 shows only one chirp signal SC. The chirp signal SC is a linear frequency modulation pulse signal, which is a sine wave whose frequency increases in a linear manner with time. In some embodiments, a frequency of the chirp signal SC increases in a non-linear manner. For the convenience of description, the linear manner is described in the following. As shown in FIG. 3, within a duration Tc (such as 40 microseconds), the chirp signal SC linearly increases from an initial frequency (such as 77 GHz) to a final frequency (such as 81 GHz) according to a slope S. The initial frequency and the final frequency may be selected from a millimetre-wave band (that is 30 GHz to 300 GHz). A difference between the initial frequency and the final frequency is a pulse bandwidth B.

Figure 5:
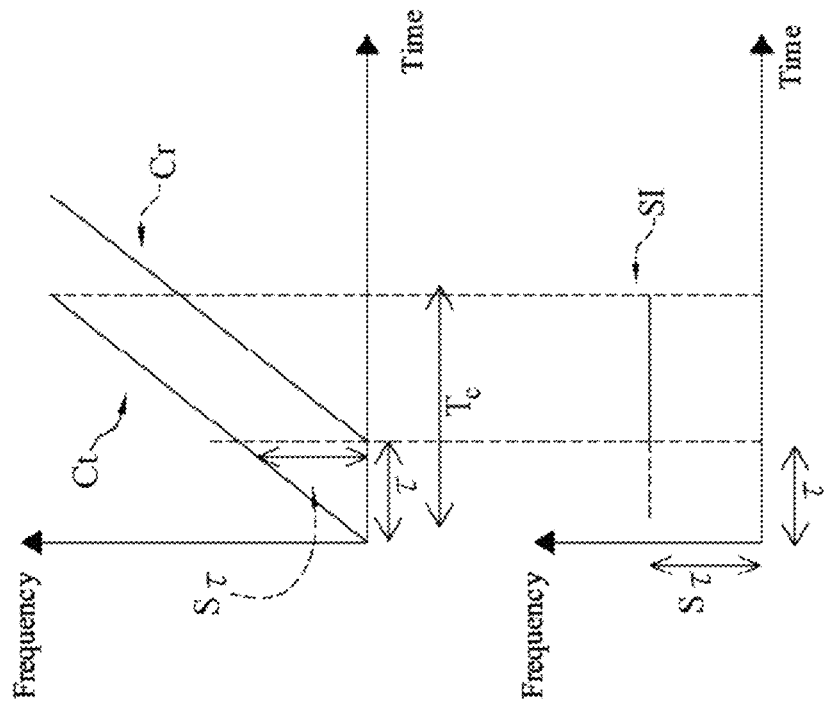
FIG. 5 is a schematic diagram illustrating the radar signal that is transmitted and received.
Figure 4:
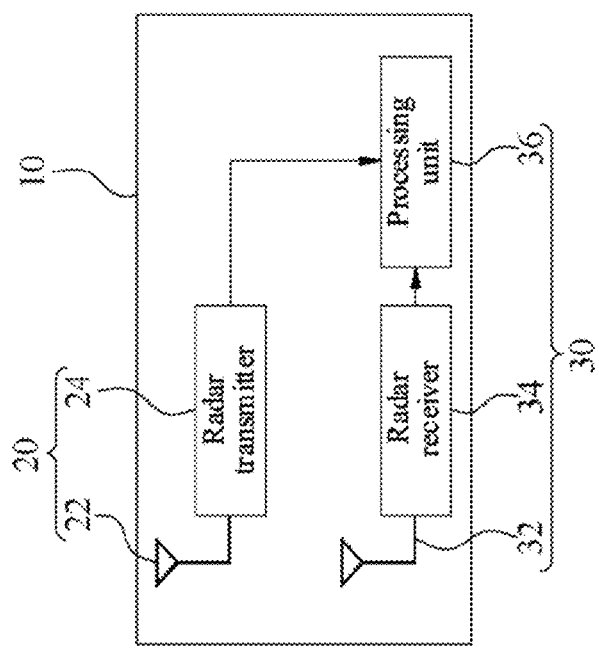
FIG. 4 is a detailed block diagram of the FMCW radar according to some embodiments.

Referring to FIG. 4 and FIG. 5 together, FIG. 4 is a detailed block diagram of the FMCW radar 10 according to some embodiments. FIG. 5 is a schematic diagram illustrating the radar signal that is transmitted and received. A transmitter 20 includes a transmitting antenna 22 and a radar transmitter 24. The radar transmitter 24 includes a signal synthesizer for generating a chirp signal Ct and transmitting the chirp signal via the transmitting antenna 22. The receiver 30 includes a receiving antenna 32, a radar receiver 34, and a processing unit 36. The receiving antenna 32 receives a reflected radar signal (a chirp signal Cr). The chirp signal Cr may be used as a delayed version of the chirp signal Ct. The radar receiver 34 includes a mixer, a low-pass filter, and an analog-to-digital converter. The mixer couples the chirp signal Ct from the radar transmitter 24 to the received chirp signal Cr, and can generate two coupled signals with a sum of frequencies of the two chirp signals Ct and Cr and a difference between the frequencies. The low-pass filter performs low-pass filtering on the coupled signal to obtain a coupled signal with the difference between the frequencies of the two chirp signals Ct and Cr, which is referred to as an "intermediate frequency signal SI". The analog-to-digital converter converts the intermediate frequency signal SI to a digital signal for the processing unit 36 to process the digital signal. The processing unit 36 may be, for example, a central processing unit (CPU), a graphics processing unit (GPU), or other programmable general-purpose or special-purpose microprocessors, a digital signal processor (DSP), a programmable controller, an application specific integrated circuit (ASIC), a programmable logic device (PLD), or other similar devices, chips, integrated circuits, and a combination thereof.

In another embodiment of the present disclosure, the FMCW radar 10 further includes a transmission module connected to the processing unit 36. The transmission module is configured to transmit, to an edge device or a cloud server at the other end, a result obtained through digital signal processing by the processing unit 36.

In another embodiment of the present disclosure, the processing unit 36 of the FMCW radar 10 only partially processes a digital signal from the analog-to-digital converter, and a result obtained through partial processing is transmitted, through the transmission module of the FMCW radar 10, to the edge device or the cloud server at the other end for subsequent processing and operations of the digital signal.

In another embodiment of the present disclosure, the processing unit 36 of the FMCW radar 10 does not perform any processing on the digital signal from the analog-to-digital converter, but the digital signal from the analog-to-digital converter is directly transmitted, through the transmission module of the FMCW radar 10, to the edge device or the cloud server at the other end for processing and operations of the digital signal.

Referring to FIG. 5, a frequency $f_0$ of the intermediate frequency signal SI may be represented as Equation 1, S is the slope, and $\tau$ is a delay time between transmitting and receiving of the radar signal. Therefore, $\tau$ may be represented as Equation 2, d is the distance between the transmitting antenna of the FMCW radar 10 and a to-be-detected object, and c is a speed of light. Equation 3 can be obtained by substituting Equation 2 into Equation 1. It may be learned from Equation 3 that the frequency $f_0$ of the intermediate frequency signal SI contains distance information (that is, a distance between the FMCW radar 10 and the to-be-detected object 50).

$$f_0 = S\tau \qquad \text{Equation 1}$$

$$\tau = 2d/c \qquad \text{Equation 2}$$

$$f_0 = 2Sd/c \qquad \text{Equation 3}$$

Figure 6:
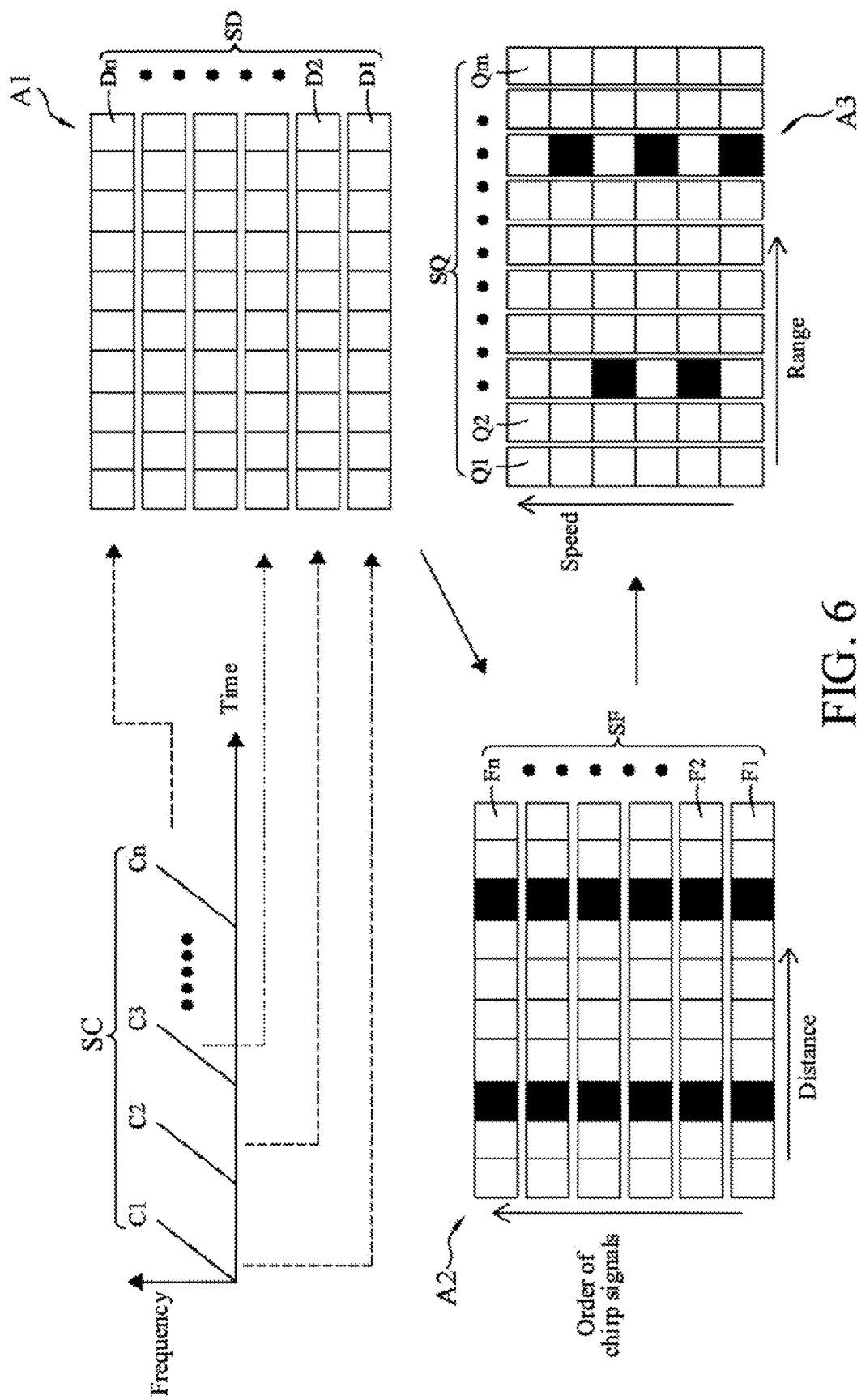
FIG. 6 is a schematic diagram of signal processing according to some embodiments.

FIG. 6 is a schematic diagram of signal processing according to some embodiments. Chirp signals SC are sequentially numbered as C1, C2, C3, . . . , Cn, where n is a positive integer. A radar receiver 34 converts, to digital signals SD (respectively represented as D1, D2, . . . , Dn, where n is a positive integer), received intermediate frequency signals SI corresponding to the chirp signals C1-Cn. Values of the digital signals SD may be represented as a one-dimensional array (row matrices). The row matrices are arranged in a longitudinal direction in sequence to form a two-dimensional array A1. It may be understood that the digital signals SD may also be arranged in a column matrix and arranged in sequence in a lateral direction, so that the two-dimensional array can also be obtained. Value of the two-dimensional array A1 represents signal strength (an amplitude). Index values in the column of the two-dimensional array A1 correspond to an order of the chirp signals SC (the digital signals SD). Index values in the row of the two-dimensional array A1 represents time, that is, the row matrix of the two-dimensional array A1 represents time domain signals.

The processing unit 36 performs fast Fourier transform (FFT) (hereinafter referred to as "distance Fourier transform") on each of the row matrices of the two-dimensional array A1 (that is, the digital signals SD) to obtain a frequency domain signal SF (respectively represented as F1, F2, . . . , Fn, where n is a positive integer), that is, the two-dimensional array A2. Therefore, the row matrix of the two-dimensional array A2 is equivalent to spectral distribution. As described above, the frequency of the intermediate frequency signal SI contains distance information. That is, the index values in the row of the two-dimensional array A2 represent distances. The values of the two-dimensional array A2 represents strength of frequencies on the spectrum, which can represent strength of radar signals reflected by the FMCW radar 10 at different distances. As shown in FIG. 6, colored boxes in the two-dimensional array A2 represent peak values (that is, the values exceed a threshold), which indicates that there is an object at a corresponding distance of the frequency. According to the frequency of the peak value, a distance between the FMCW radar 10 and the to-be-detected object 50 can be calculated.

Since an interval between the chirp signals SC is very short (for example, tens of microseconds), relatively, a position of the same object that reflects the chirp signals SC is basically constant. Therefore, each of the frequency domain signals SF has a colored box corresponding to the same distance, and a column of colored boxes is presented. As shown in FIG. 6, in this example, two columns of colored boxes are presented. Although the frequency domain signals SF have a peak value in the same column, a slight movement change cannot cause an obvious change in the frequency, but a phase composition causes an obvious influence. The index values in the column of the two-dimensional array A2 correspond to the order of the frequency domain signals SF (the chirp signals SC), which is a time order. Therefore, the column matrices of the two-dimensional array A2 may be used as time domain signals. The processing unit 36 performs fast Fourier transform (hereinafter referred to as "Doppler Fourier transform") on the column matrices of the two-dimensional array A2, so that phase frequency domain signals SQ (respectively represented as Q1, Q2, . . . , Qm, where m is a positive integer) can be respectively obtained, that is, a two-dimensional array A3. Therefore, a column matrix of the two-dimensional array A3 is equivalent to phase spectrum distribution. A phase $\phi_0$ of the intermediate frequency signal SI may be represented as Equation 4, and after substituted into Equation 2, may be represented as Equation 5, and $\lambda$ is a wavelength. According to Equation 5, Equation 6 can be derived, where v is a speed, $\Delta\phi$ is a phase difference between two adjacent chirp signals (Cn−1, Cn), and $\Delta t$ is a time difference between two adjacent chirp signals SC. It may be learned from Equation 6 that the phase of the intermediate frequency signal SI contains movement information (a speed). Therefore, the index values in the column of the two-dimensional array A3 represent speeds. According to the phase frequency domain signal SQ, a moving speed of the to-be-detected object 50 or a frequency of a periodic movement can be calculated, and characterization information of the to-be-detected object 50 (such as movement information and physiological information (such as a respiratory rate and a heartbeat frequency)) can be obtained. The two-dimensional array A3 in FIG. 6 is given by way of example. In two columns, there are two colored boxes and three colored boxes, which indicates that there are at least two to-be-detected objects 50 at two different distances from the FMCW radar 10, and the speed (frequency) corresponding to each of the colored boxes is the characterization information of the corresponding to-be-detected object 50.

$$\phi_0 = 2\pi f_0 \tau \quad \text{Equation 4}$$

$$\phi_0 = \frac{4\pi d}{\lambda} \quad \text{Equation 5}$$

$$v = \frac{\lambda \Delta \phi}{4\pi \Delta t} \quad \text{Equation 6}$$

In some embodiments, the processing unit 36 may not perform fast Fourier transform on the entire two-dimensional array A2, but only perform fast Fourier transform on the same peak (two column matrices represented as colored boxes) of the frequency domain signals SF to reduce the number of operations and save the calculation time.

From the above description, it may be understood that by performing signal coupling, analog-digital conversion, and digital signal processing on the received chirp signals Cr, the distance information and the characterization information can be obtained. However, in an indoor environment, the radar signal is easily affected by other factors other than the detection area 40, which may cause erroneous determination of information. For example, the signal is subject to static environment interference from reflection of a wall or a floor, and the signal is subject to dynamic environment interference from disturbance of other moving objects (such as an electric fan and a curtain). Therefore, after the digital signals SD are obtained, and before signal processing such as the above distance Fourier transform and Doppler Fourier transform, the following method for processing digital signals can be performed to solve the problem of poor signals caused by the environmental interference.

Figure 7:
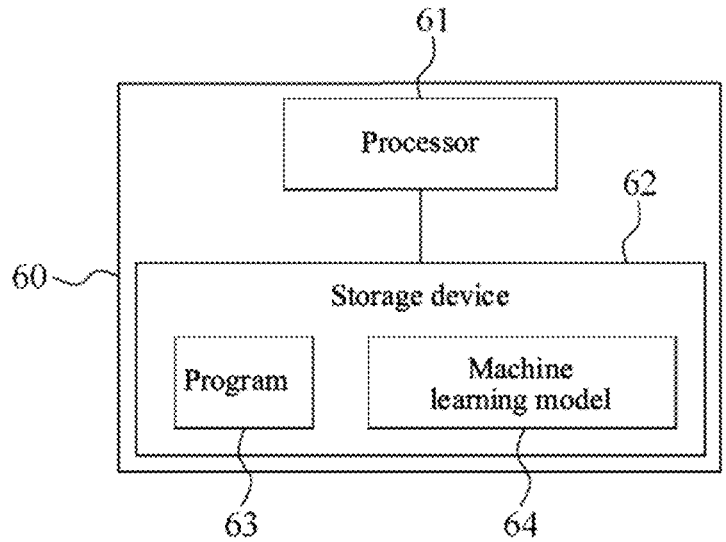
FIG. 7 is a schematic block diagram of a signal processing device according to some embodiments.
Figure 8:
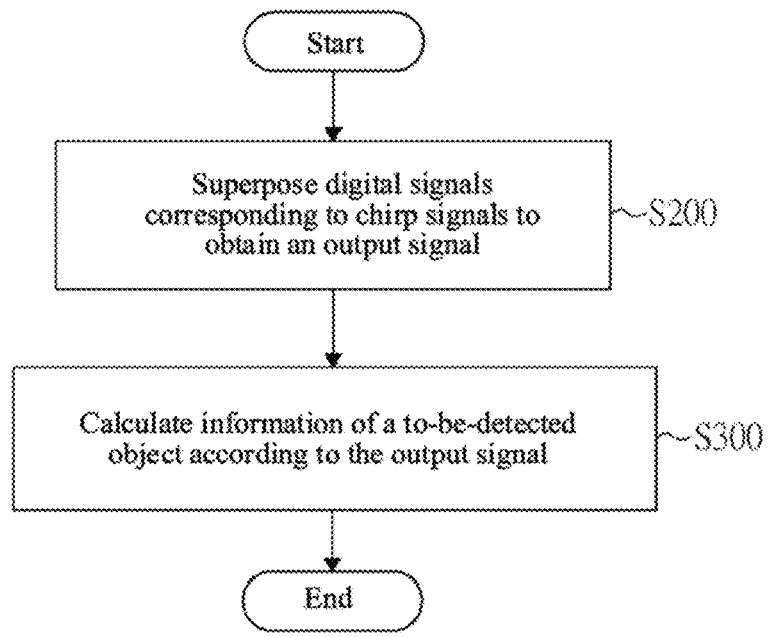
FIG. 8 is a flowchart of a method for processing digital signals according to an embodiment.

Referring to FIG. 7 and FIG. 8 together, FIG. 7 is a schematic block diagram of a signal processing device 60 according to some embodiments. FIG. 8 is a flowchart of a method for processing digital signals according to an embodiment. The signal processing device 60 includes a processor 61 and a storage device 62. The storage device 62 is a computer-readable storage medium for storing a program 63 executed by the processor 61 to perform the method for processing digital signals. In some embodiments, the signal processing device 60 is a Doppler radar (such as the above FMCW radar 10), and the processor 61 is the above processing unit 36. In some embodiments, the Doppler radar is a continuous wave (CW) radar or an ultra-wideband (UWB) radar. In some embodiments, the signal processing device 60 is an edge device or a cloud server, that is, after the FMCW radar 10 obtains digital signals SD, the digital signals SD are to be transmitted to the edge device or the cloud server and processed by the edge device or the cloud server.

Figure 9:
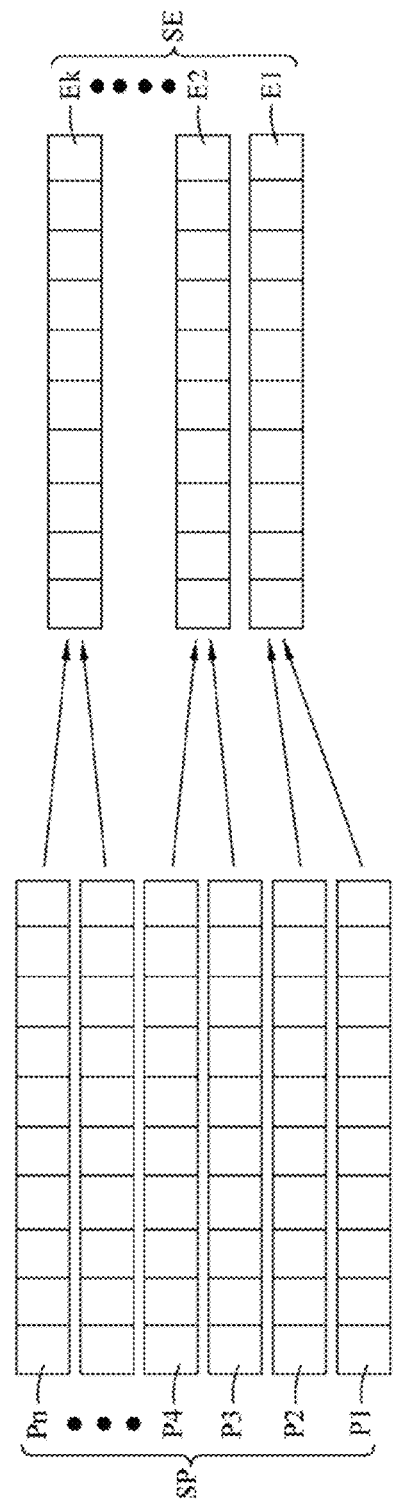
FIG. 9 is a schematic diagram illustrating signal superposition.

Referring to FIG. 7 to FIG. 9 together, FIG. 9 is a schematic diagram illustrating signal superposition. A receiving terminal of the Doppler radar (the FMCW radar 10) converts, to digital signals P1-Pn, the received intermediate frequency signals SI corresponding to the chirp signals C1-Cn. In a process S200, the digital signals SP corresponding to the chirp signals SC are superposed to obtain output signals SE (as shown in FIG. 9, which are respectively represented as E1-Ek, where k is a positive integer). An example shown in FIG. 9 is given for description. Every two adjacent digital signals SP are superposed to obtain the output signal SE. For example, the digital signals P1 and P2 are superposed to obtain the output signal E1, and the digital signals P3 and P4 are superposed to obtain the output signal E2. Random noise caused by the environment may be averaged by superposing the signals, so that a signal-to-noise ratio (SNR) can be increased. In addition, after the signals are superposed, a plurality of one-dimensional arrays may be merged into one one-dimensional array, which can greatly reduce an amount of to-be-processed data to accelerate the processing speed. Although the superposition of two adjacent digital signals SP is given by way of example, the embodiment of the present invention is not limited thereto. Alternatively, more than two adjacent digital signals SP may be superposed.

In some embodiments, the digital signals SP superposed with each other correspond to a plurality of chirp signals SC in the same frame. In some other embodiments, the digital signals SP superposed with each other correspond to the plurality of chirp signals SC in a plurality of adjacent frames. The plurality of adjacent frames may be more than two frames.

Process S300: According to the superposed output signals SE, the above distance Fourier transform and Doppler Fourier transform can be performed, and information such as distance information and characterization information (movement information and physiological information) of the to-be-detected object 50 can be calculated.

In the above example, the transmitter 20 has one transmitting antenna 22, and the receiver 30 has one receiving antenna 32. However, in some embodiments, the transmitter 20 may have a plurality of transmitting antennas 22. Similarly, in some embodiments, the receiver 30 may have a plurality of receiving antennas 32.

Figure 10:
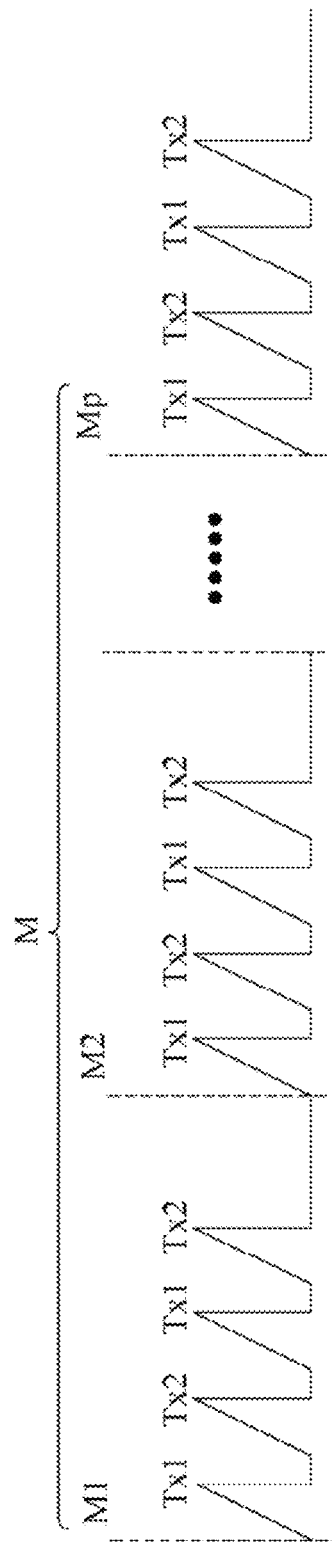
FIG. 10 is a schematic diagram illustrating chirp signals.

FIG. 10 is a schematic diagram illustrating chirp signals SC. For example, the transmitter 20 has two transmitting antennas 22. The chirp signals SC are receptively marked as Tx1 and Tx2, which respectively represent the chirp signals SC transmitted by a first transmitting antenna 22 and a second transmitting antenna 22. The radar signal is defined to have a plurality of frames M (respectively represented as M1-Mp, where p is a positive integer). Each of the frames M includes a plurality of chirp signals SC. For example, each of the transmitting antennas 22 alternately transmits the chirp signals Tx1 and Tx2 and transmits four chirp signals SC in total. A period of the frame M may be, for example, 20 milliseconds. Within the period of each of the frames M, the processor 61 performs the above method for processing digital signals according to the chirp signals SC in each of the frames M. In other words, the processor 61 superposes the digital signals SP corresponding to the chirp signals SC in the same frame M to obtain the output signal SE, and the process S300 is performed. For example, within the period of the frame M1, the method for processing digital signals is performed once according to the two chirp signals Tx1 and the two chirp signals Tx2 in the frame M1. Within the period of the frame M2, the method for processing digital signals is performed once according to the two chirp signals Tx1 and the two chirp signals Tx2 in the frame M2. Different methods for signal superposition are described below.

Figure 11:
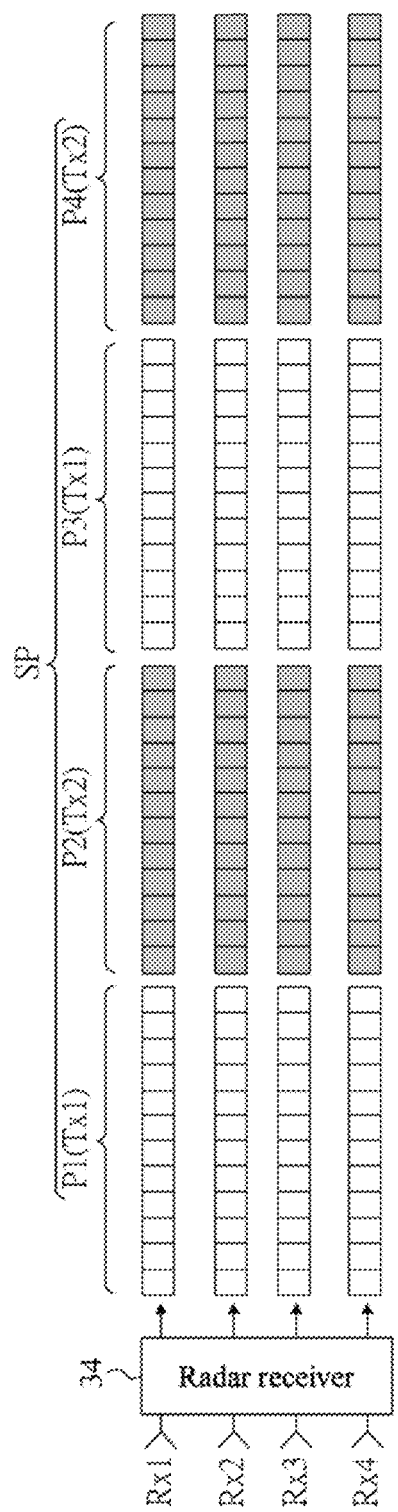
FIG. 11 is a schematic diagram illustrating receiving the signals in FIG. 10.

FIG. 11 is a schematic diagram illustrating receiving the signal of FIG. 10. For example, a receiver 30 having four receiving antennas Rx1, Rx2, Rx3, and Rx4 receives the radar signal shown in FIG. 10. The chirp signals Tx1 and Tx2 are received via each of receiving antennas Rx1, Rx2, Rx3, and Rx4 and are converted to digital signals SP by a radar receiver 34 (only four digital signals P1-P4 in one frame M are used for description). A first digital signal P1 corresponds to a first chirp signal Tx1 transmitted by the first transmitting antenna 22. A second digital signal P2 corresponds to a first chirp signal Tx2 transmitted by the second transmitting antenna 22. A third digital signal P3 corresponds to a second chirp signal Tx1 transmitted by the first transmitting antenna 22. A fourth digital signal P4 corresponds to a second chirp signal Tx2 transmitted by the second transmitting antenna 22.

Figure 12:
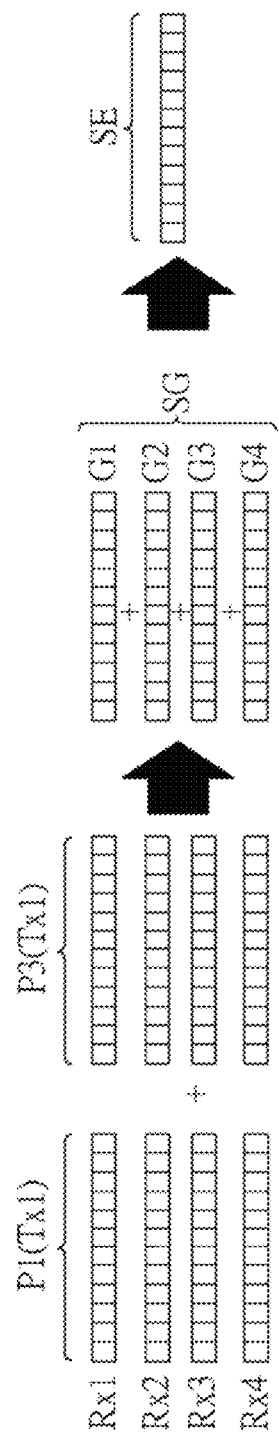
FIG. 12 is another schematic diagram illustrating signal superposition.

FIG. 12 is another schematic diagram illustrating signal superposition. The processor 61 may superpose the digital signals SP corresponding to the chirp signals SC respectively received by the receiving antennas Rx1-Rx4 from the same transmitting antenna 22. For example, the first digital signal P1 and the third digital signal P3 both correspond to the chirp signal Tx1 from the first transmitting antenna 22, both of which are superposed to obtain superposed signals SG (respectively represented as G1-G4). The processor 61 further superposes the signals (G1-G4) corresponding to the receiving antennas Rx1-Rx4 in the superposed signals SG to obtain an output signal SE. Stated another way, the processor 61 superposes the digital signals SP corresponding to the chirp signals SC received by the receiving antennas Rx1-Rx4 from the same transmitting antenna 22 to obtain the output signal SE. In some embodiments, the processor 61 superposes the digital signals SP corresponding to the chirp signals SC from other transmitting antennas 22 (for example, the chirp signal Tx2 from the second transmitting antenna 22).

In some embodiments, the processor 61 does not superpose the superposed signals SG corresponding to the receiving antennas Rx1-Rx4, but selects the superposed signal G1, G2, G3, or G4 corresponding to one of the receiving antennas Rx1-Rx4 as the output signal SE. In other words, the digital signals SP corresponding to the chirp signals SC received by one of the receiving antennas Rx1-Rx4 from the same transmitting antenna 22 are selected to be superposed to obtain the output signal SE.

Figure 13:
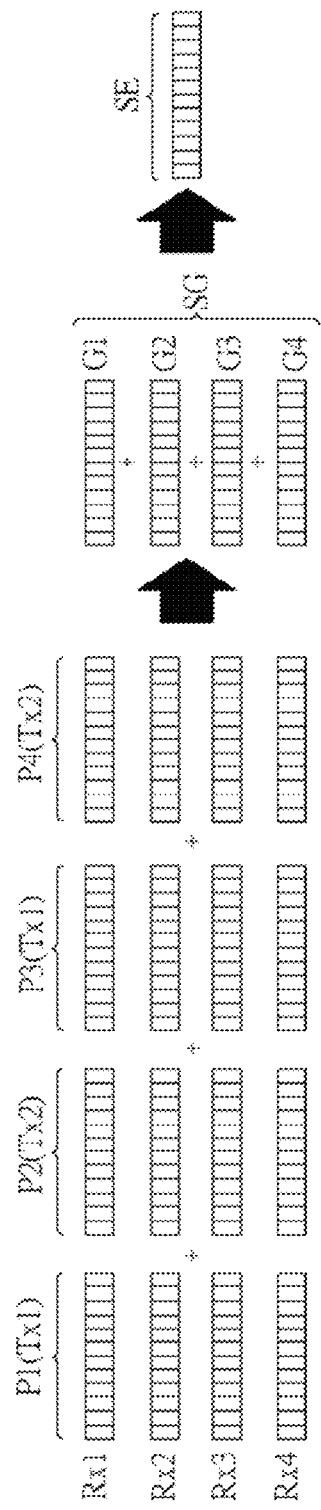
FIG. 13 is still another schematic diagram illustrating signal superposition.

FIG. 13 is still another schematic diagram illustrating signal superposition. In addition to only superposing the digital signals SP corresponding to the chirp signals SC from the same transmitting antenna 22 shown in FIG. 12, the processor 61 may also superpose the digital signals SP corresponding to the chirp signals SC from different transmitting antennas 22 (that is, at least two transmitting antennas 22). For example, although the digital signals P1-P4 are from different transmitting antennas 22, the processor 61 superposes the digital signals P1-P4 corresponding to the chirp signals SC received by each of the receiving antennas Rx1-Rx4 to obtain the superposed signals SG (respectively represented as G1-G4). The processor 61 further superposes the signals (G1-G4) corresponding to the receiving antennas Rx1-Rx4 in the superposed signals SG to obtain an output signal SE. Stated another way, the processor 61 superposes the digital signals SP corresponding to the chirp signals SC received by the receiving antennas Rx1 to Rx4 from different transmitting antennas 22 (that is, at least two transmitting antennas 22) to obtain an output signal SE.

Figure 14:
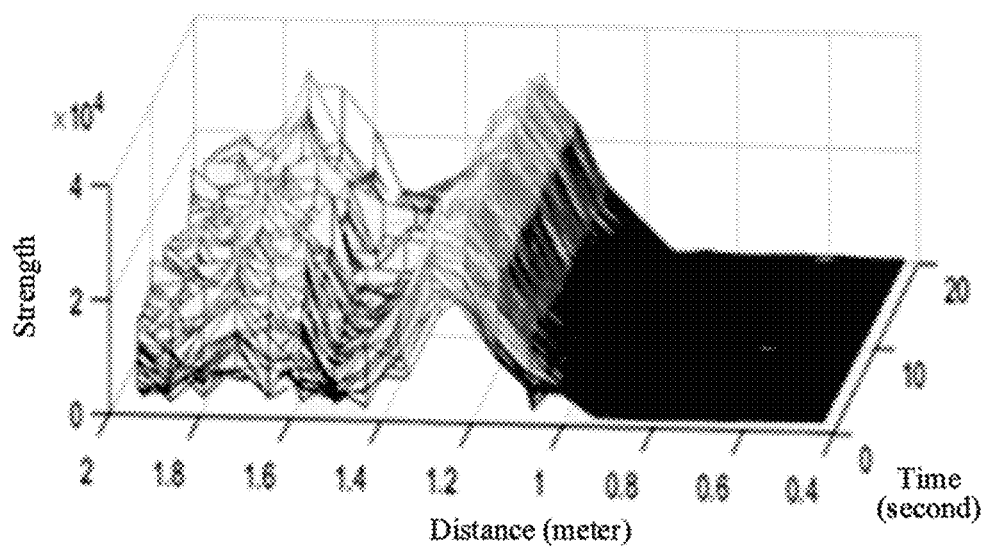
FIG. 14 is a schematic diagram illustrating digital signals without being superposed and on which distance Fourier transform is performed in a static environment.
Figure 15:
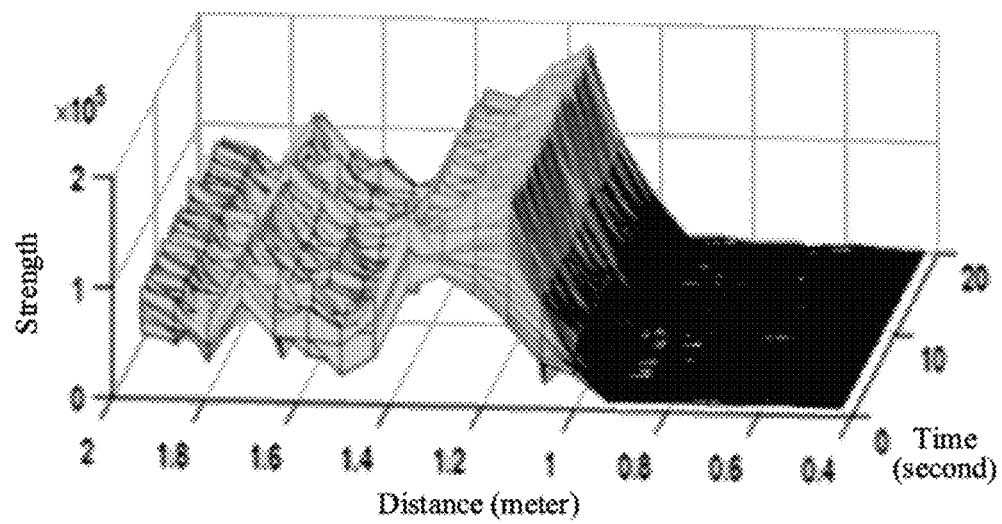
FIG. 15 is a schematic diagram illustrating the digital signals that are superposed in the manner shown in FIG. 13 and on which distance Fourier transform is performed in the static environment.

Referring to FIG. 14 and FIG. 15, FIG. 14 is a schematic diagram illustrating digital signals SP without being superposed and on which distance Fourier transform is performed in a static environment. FIG. 15 is a schematic diagram illustrating the digital signals that are superposed in the manner shown in FIG. 13 and on which the distance Fourier transform is performed in the static environment. A horizontal axis represents the distance information obtained through distance Fourier transform, a longitudinal axis represents signal strength, and a vertical axis represents time. It can be seen that after the signals are superposed, interference noise of the static environment on the left side is obviously reduced.

In some embodiments, the processor 61 does not superpose the superposed signals SG corresponding to the receiving antennas Rx1-Rx4, but selects the superposed signal G1, G2, G3, or G4 corresponding to one of the receiving antennas Rx1-Rx4 as the output signal SE. In other words, the digital signals SP corresponding to the chirp signals SC received by one of the receiving antennas Rx1-Rx4 from different transmitting antennas 22 (that is, at least two transmitting antennas 22) are superposed to obtain an output signal SE.

In some embodiments, although the chirp signals SC in the same frame M are superposed for description above, the processor 61 may also superpose the digital signals SP corresponding to the chirp signals SC in two adjacent frames M to obtain the output signal SE. In some embodiments, the processor 61 may also superpose the digital signals SP corresponding to the chirp signals SC in at least three adjacent frames M to obtain the output signal SE. As described above, the method of superposing the digital signals SP in at least two adjacent frames M may be superposing the digital signals SP corresponding to the chirp signals SC from the same transmitting antenna 22, or superposing the digital signals SP corresponding to the chirp signals SC from different transmitting antennas 22 are superposed. Details are not described herein again. As described above, one of the superposed signals (the superposed signals SG) may be selected as the output signal SE. alternatively, the superposed signals SG are superposed to obtain the output signal SE. Details are not described herein again. Since the digital signals SP corresponding to the chirp signals SC in at least two adjacent frames M are superposed, the method for processing digital signals is performed once for every at least two frames M.

Figure 16:
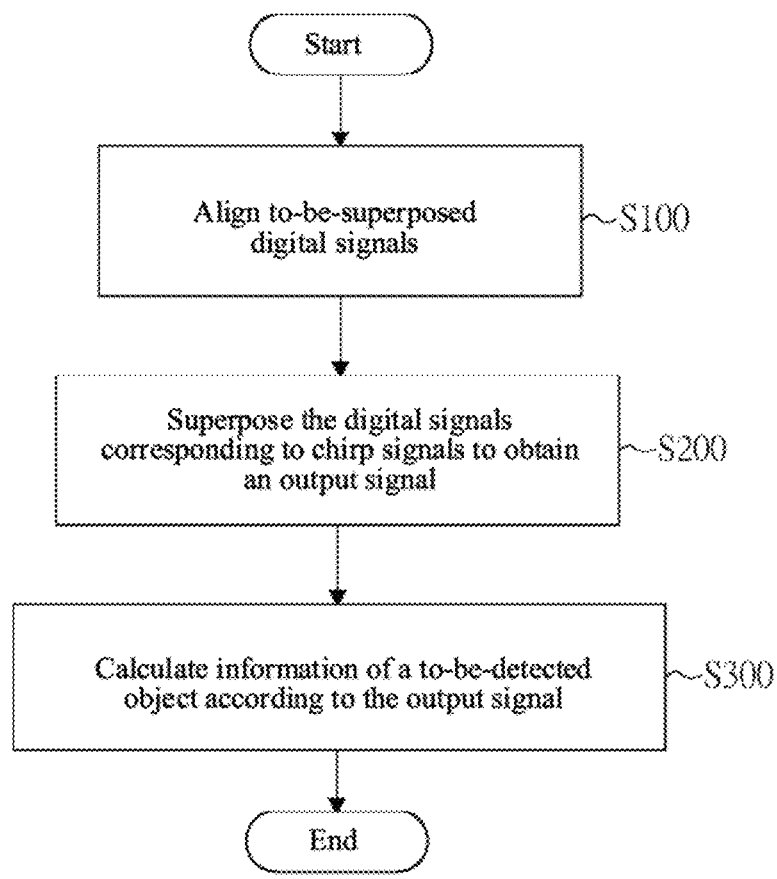
FIG. 16 is a flowchart of a method for processing digital signals according to another embodiment.

FIG. 16 is a flowchart of a method for processing digital signals according to another embodiment. Different from FIG. 8, before the process S200, a process S100 is performed to align the to-be-superposed digital signals SP. In this way, a phase delay between the digital signals SP can be corrected. In some embodiments, if the phase delay between the to-be-superposed digital signals SP is within an allowable range, the process S100 may not be performed. For example, if the processor 61 superposes the chirp signals SC in the same frame M, the phase delay between the digital signals is generally within the allowable range, and the process S100 may not be performed. If the processor 61 superposes the chirp signals SC in at least two adjacent frames M, and the phase delay between the digital signals exceeds the allowable range, the process S100 is performed before the process S200.

Figure 17:
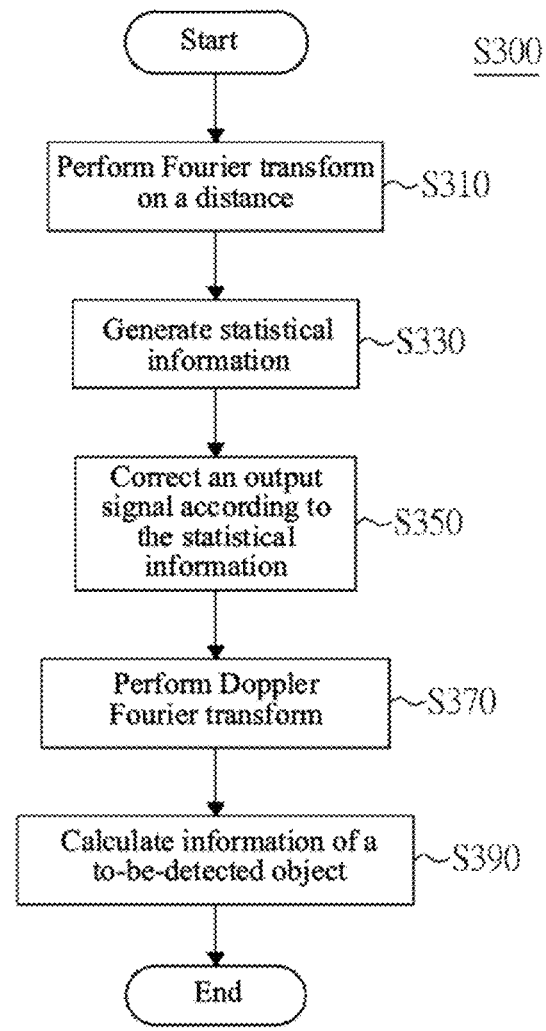
FIG. 17 is a flowchart of calculating information of a to-be-detected object according to an embodiment.

FIG. 17 is a flowchart of calculating information of the to-be-detected object according to an embodiment. In addition to the distance Fourier transform (step S310), the Doppler Fourier transform (step S370), and the calculation of information of the to-be-detected object 50 (step S390), the process S300 further includes steps S330 and S350.

Figure 18:
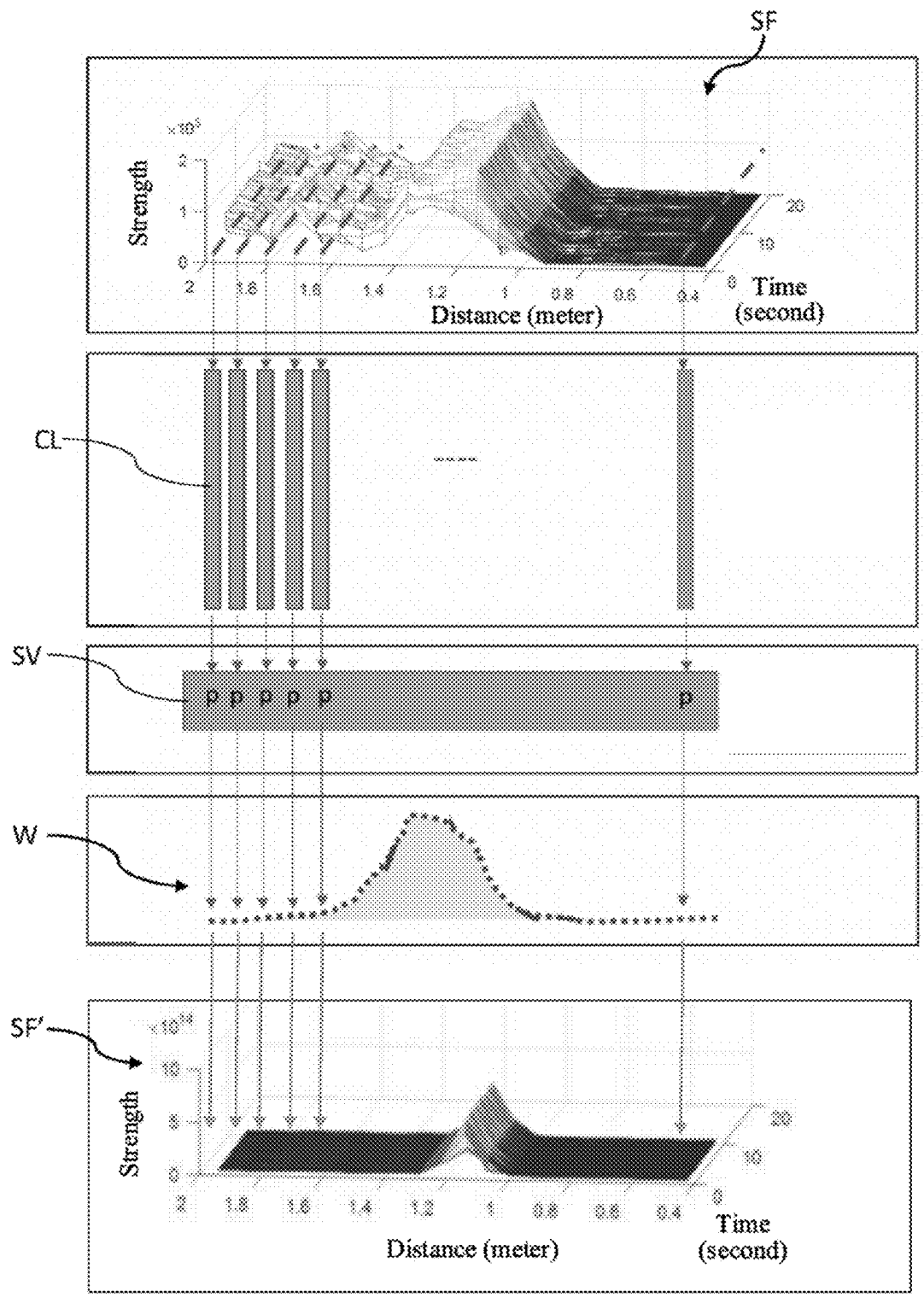
FIG. 18 is a schematic diagram illustrating generation of statistical information.

Referring to FIG. 17 and FIG. 18 together, FIG. 18 is a schematic diagram illustrating generation of statistical information. After a frequency domain signal SF is obtained through step S310 (a horizontal axis represents distance information obtained after distance Fourier transform, a longitudinal axis represents signal strength, and a vertical axis represents time. In case of representation in two dimensions, it is equivalent to the two-dimensional array A2 shown in FIG. 6), step S330 is performed. In step S330, the processor 61 may generate statistical information SV according to the frequency domain signal SF. Specifically, calculation of the statistical information SV is performed on the frequency domain signal SF according to the time axis. Through the statistical information SV, signal characteristics may be analyzed to facilitate distinction between dynamic interference and an object signal source in an environment. The statistical information SV may be, for example, an absolute sum of squares, an absolute maximum, a standard deviation, or a variance. In detail, the processor 61 calculates the statistical information SV for each of the column matrices CL of the two-dimensional array A2, that is, counts the signal strength in a time sequence at each distance. For example, a standard deviation p is calculated for each of the column matrices CL. As shown in FIG. 18, a distribution curve W depicted according to the standard deviations p is displayed, which can be used as a mask for the subsequent step S350 to correct the signal.

In step S350, the processor 61 corrects the signal according to the statistical information SV. In other words, the frequency domain signal SF is normalized according to the statistical information SV. For example, the signals in the time sequence at each distance is multiplied by the corresponding statistical information SV (such as the standard deviation p), that is, each of the column matrices CL of the two-dimensional array A2 is multiplied by the statistical information SV (such as the standard deviation p) corresponding to each of the column matrices CL. As shown in FIG. 18, a corrected frequency domain signal SF' is displayed. More accurate information such as distance information and characterization information (such as movement information and physiological information) of the to-be-detected object 50 can be calculated according to the corrected frequency domain signal SF' (step S390).

Figure 19A:
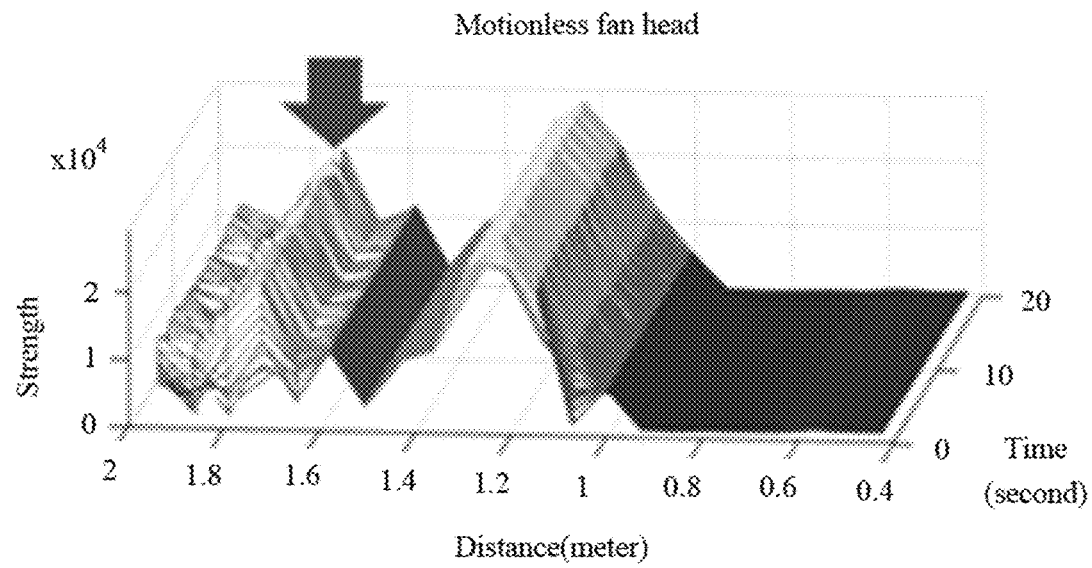
FIG. 19A to FIG. 19E are schematic diagrams illustrating frequency domain signals under different environmental interference.
Figure 19B:
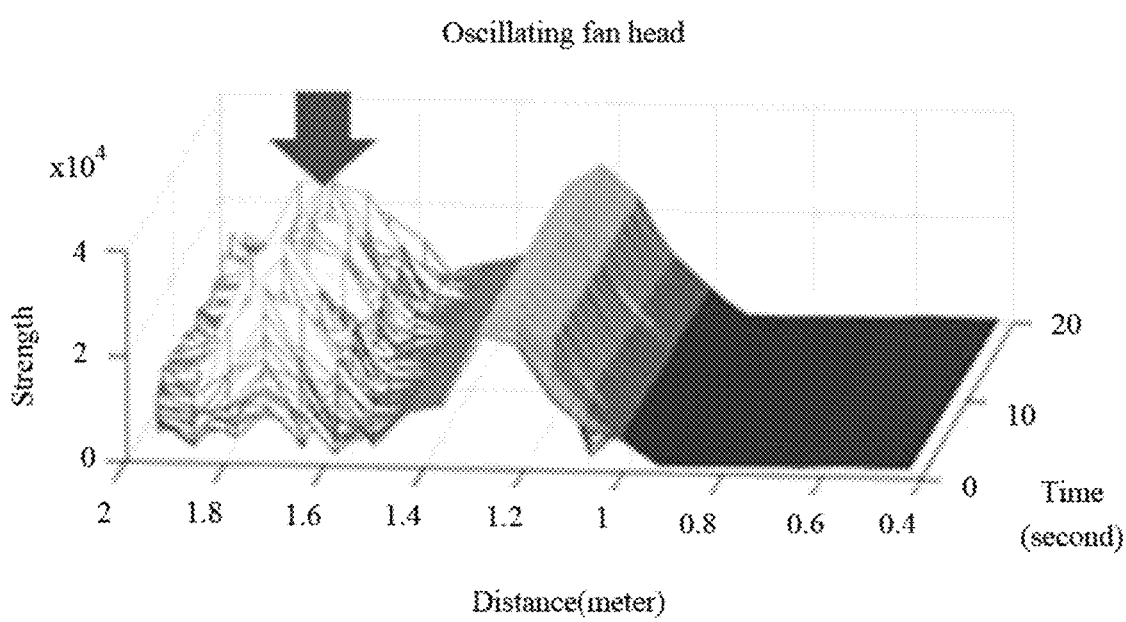
Figure 19C:
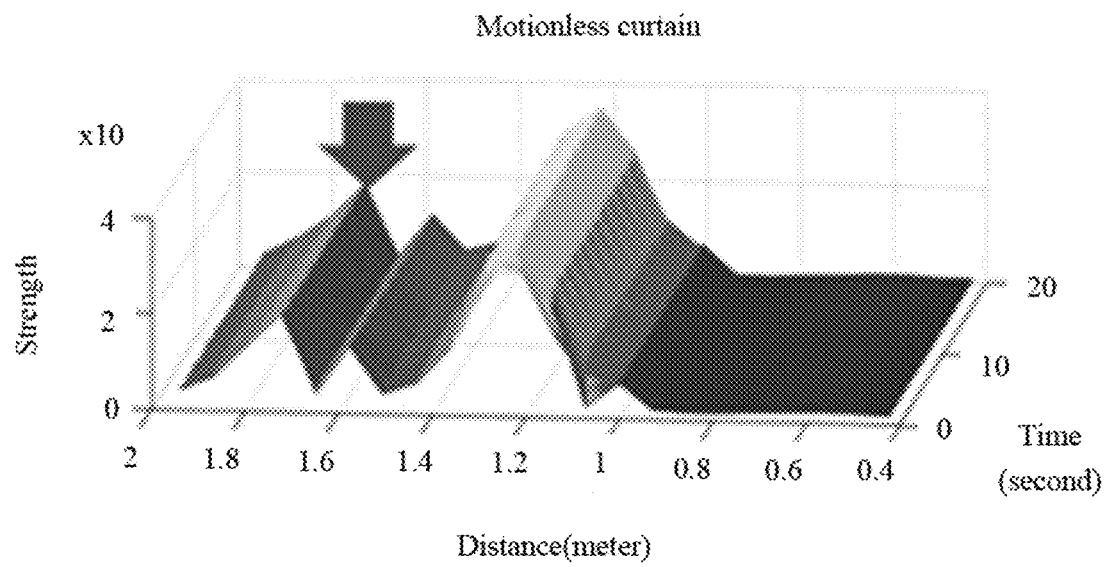
Figure 19D:
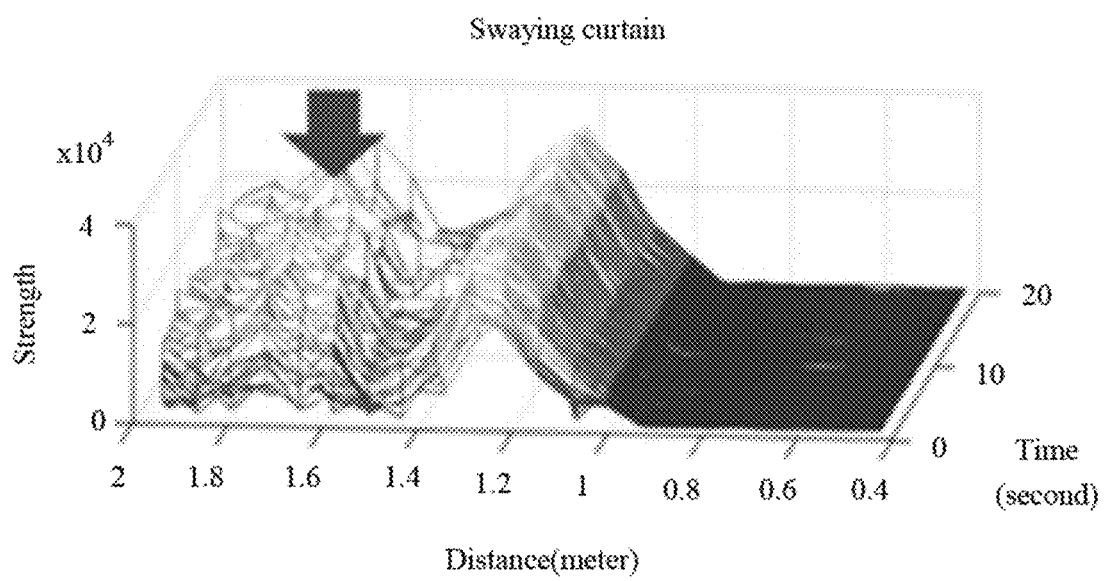
Figure 19E:
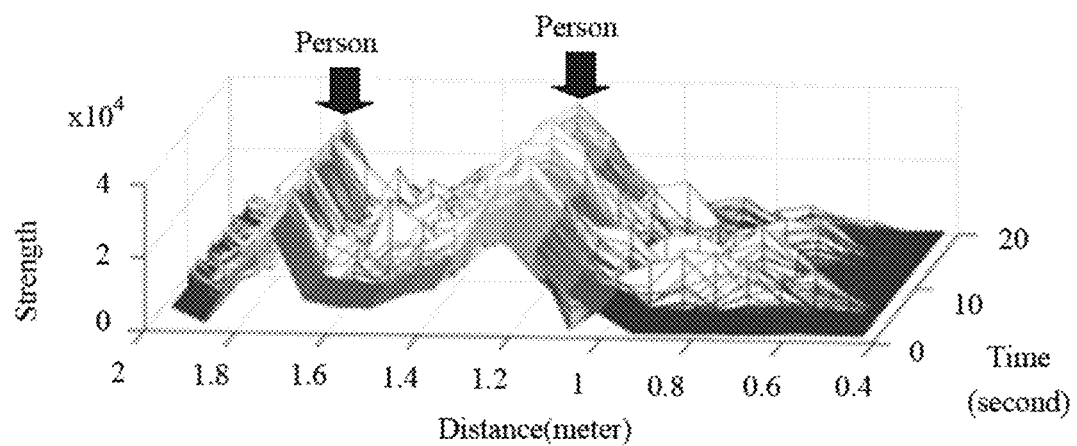
Figure 20A:
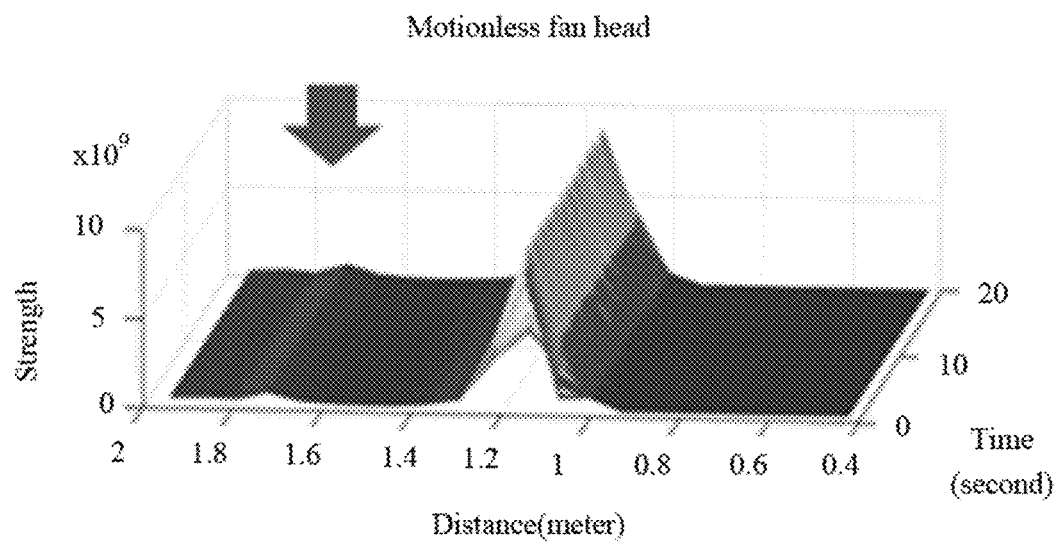
FIG. 20A to FIG. 20E are schematic diagrams illustrating corrected frequency domain signals under different environmental interference.
Figure 20B:
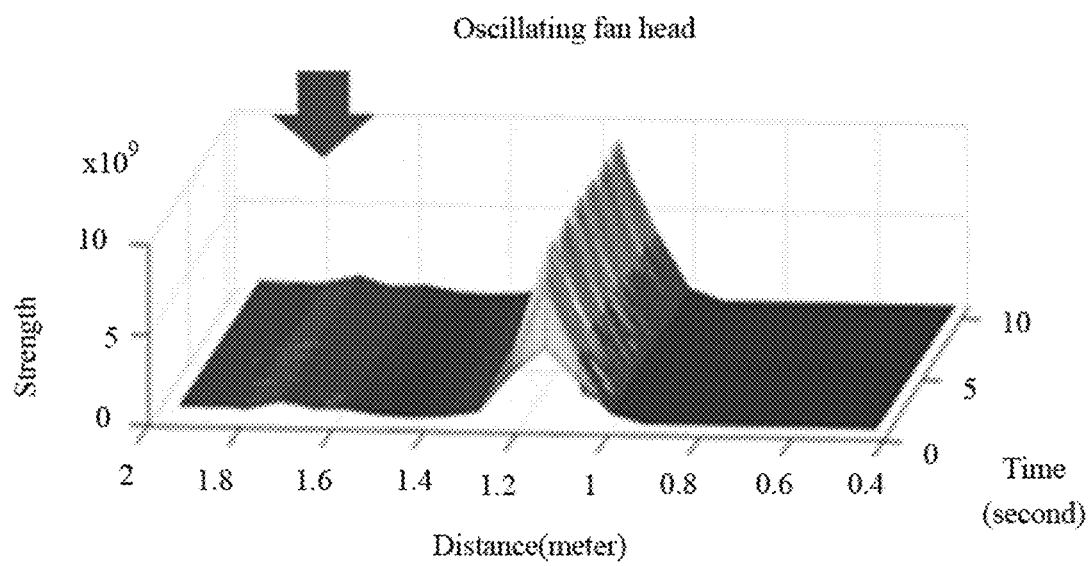
Figure 20C:
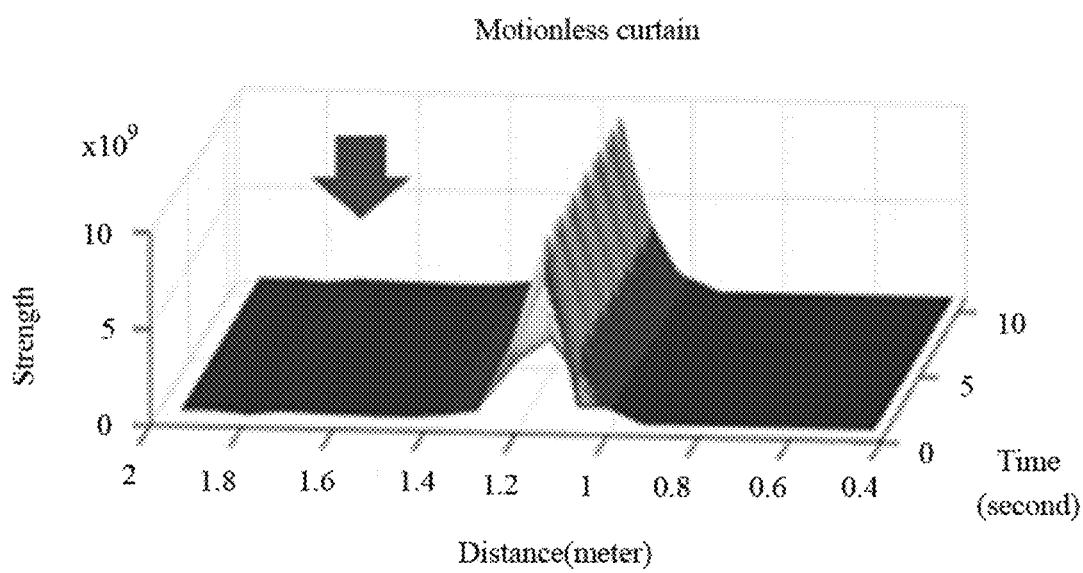
Figure 20D:
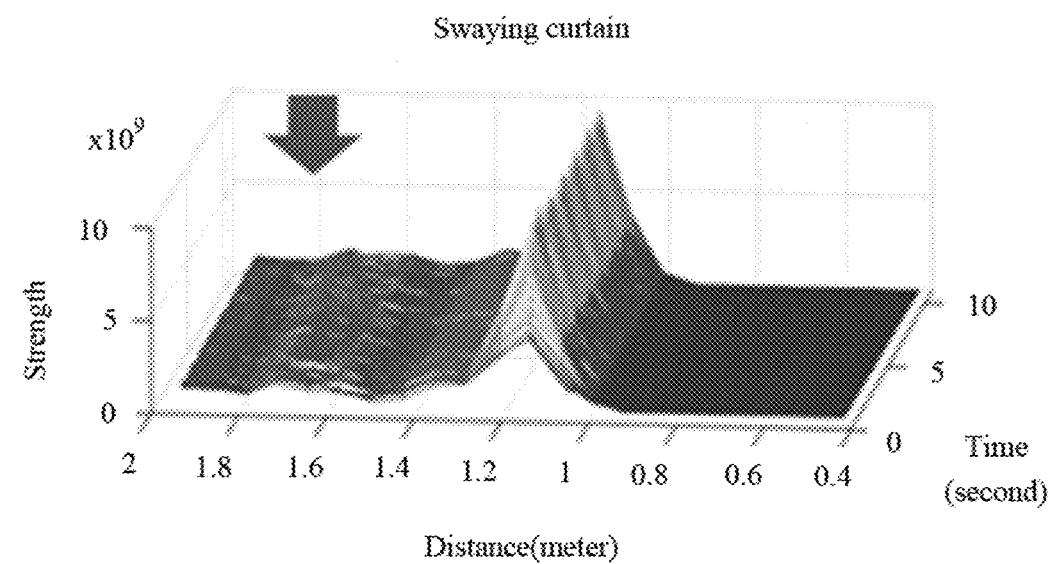
Figure 20E:
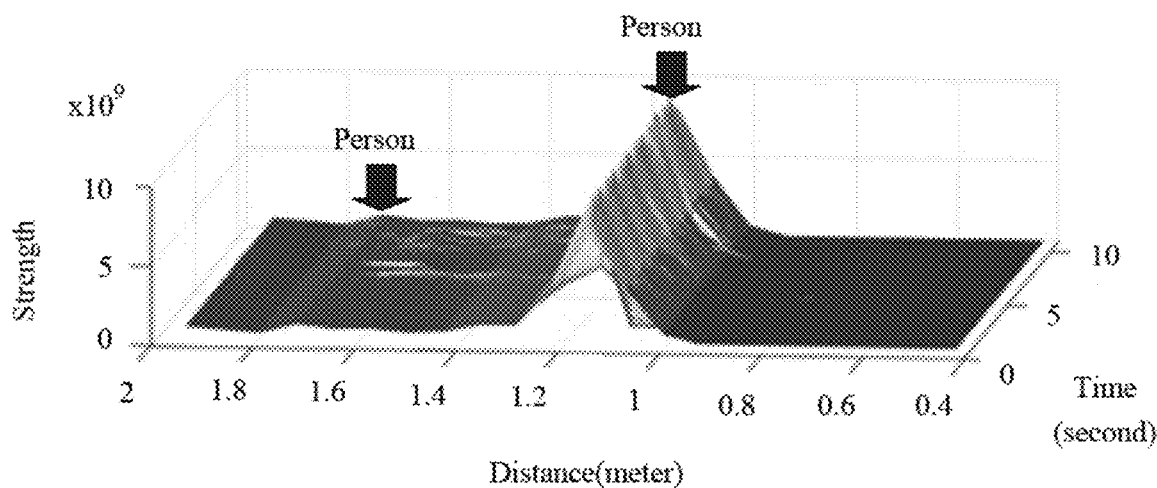

Referring to FIG. 19A to FIG. 19E and FIG. 20A to FIG. 20E together, FIG. 19A to FIG. 19E are schematic diagrams illustrating frequency-domain signals SF under different environmental interference. FIG. 20A to FIG. 20E are schematic diagrams illustrating corrected frequency domain signals SF' under different environmental interference. FIG. 19A and FIG. 20A show environmental interference caused when a fan rotates but does not oscillate. FIG. 19B and FIG. 20B show environmental interference caused when a fan rotates and oscillates. FIG. 19C and FIG. 20C show environmental interference caused when a curtain is motionless. FIG. 19D and FIG. 20D show environmental interference caused when a curtain sways. FIG. 19E and FIG. 20E show environmental interference caused when a person moves. It can be clearly seen that through the above signal correction, the dynamic environment interference can be eliminated indeed.

Figure 21A:
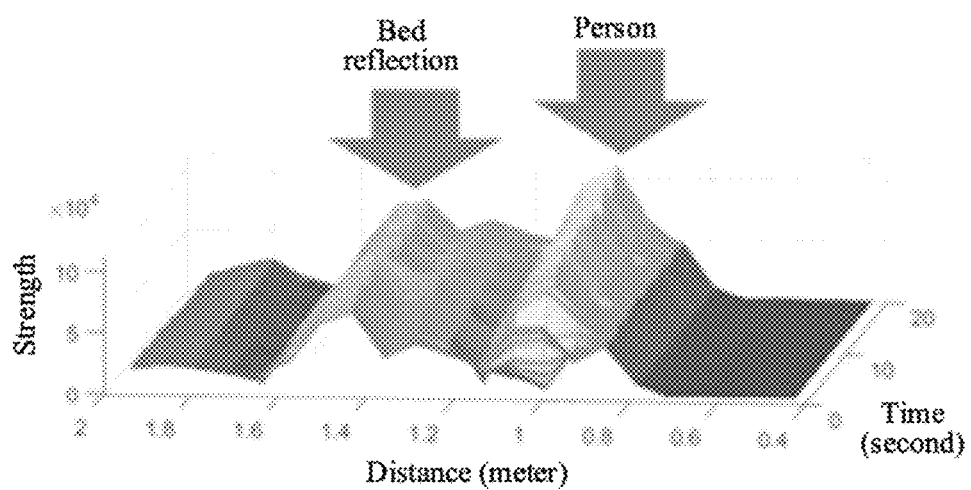
FIG. 21A is a schematic diagram illustrating a frequency domain signal of a to-be-detected object lying on its side.
Figure 21B:
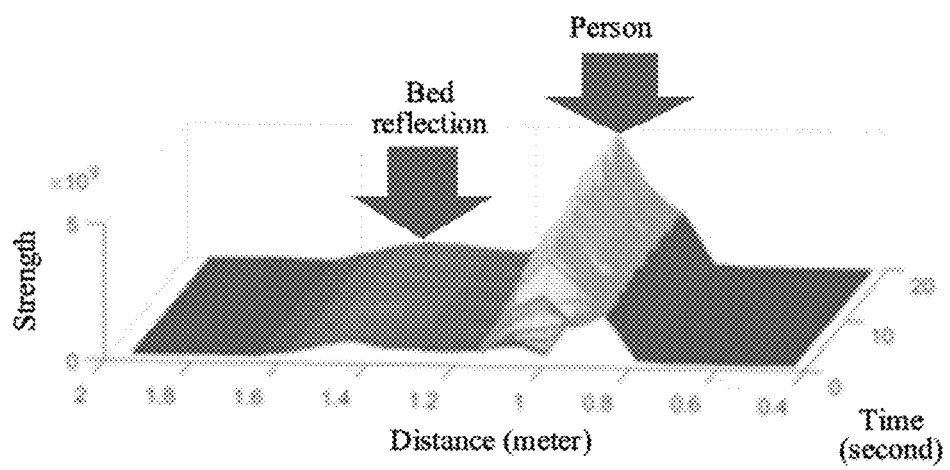
FIG. 21B is a schematic diagram illustrating a corrected frequency domain signal of the to-be-detected object lying on its side.

Referring to FIG. 21A and FIG. 21B together, FIG. 21A is a schematic diagram illustrating the frequency domain signal SF of the to-be-detected object 50 lying on its side. FIG. 21B is a schematic diagram illustrating a corrected frequency domain signal SF' of the to-be-detected object 50 lying on its side. Through the above signal correction, signal interference from reflection of a bed caused by different postures (for example, lying on the side) of the to-be-detected object 50 can also be eliminated, and therefore influences caused by different sleeping postures can also be effectively suppressed.

Figure 22:
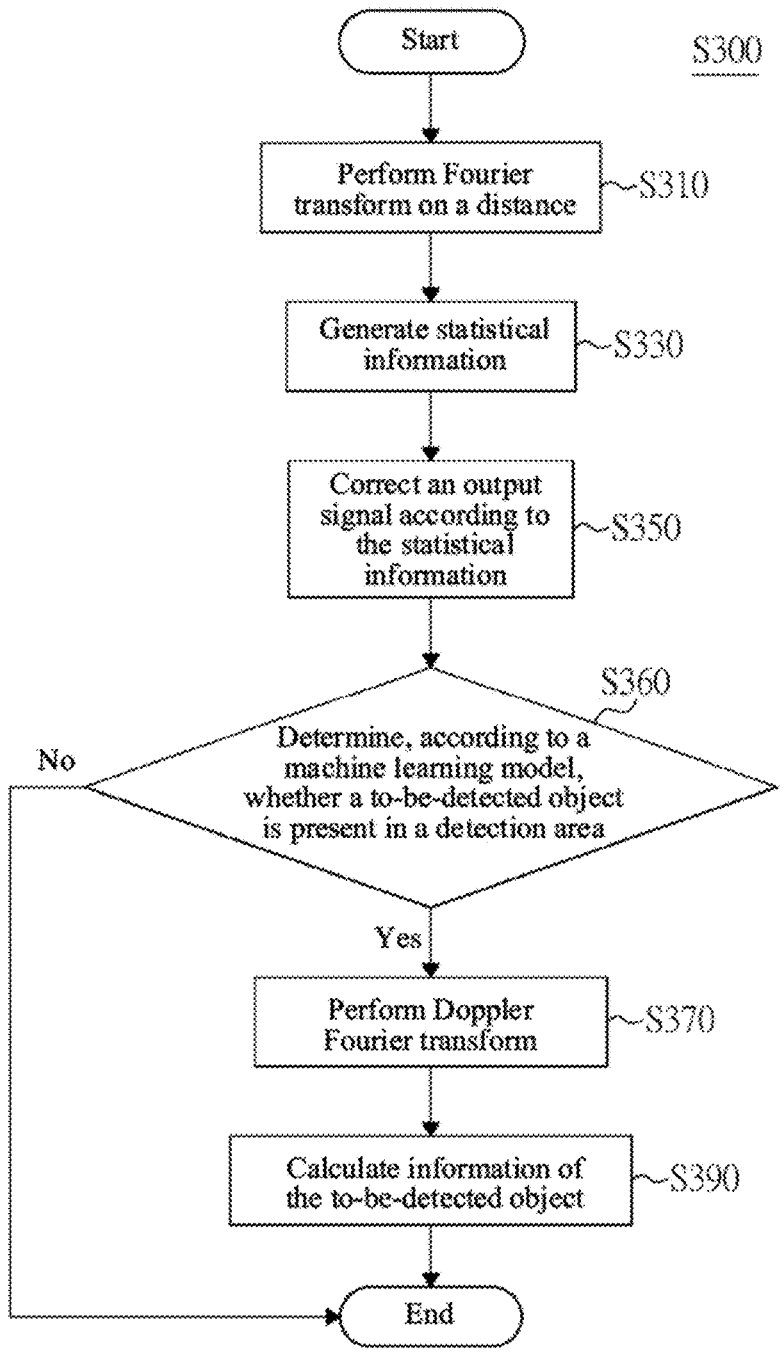
FIG. 22 is a flowchart of calculating information of the to-be-detected object according to another embodiment.

Referring to FIG. 7 and FIG. 22 together, FIG. 22 is a flowchart of calculating information of the to-be-detected object according to another embodiment. The storage device 62 further stores a machine learning model 64, which is trained through the above corrected signals obtained in different situations. The different situations include: under various environmental conditions (for example, the fan rotates, the curtain sways, and the like), the to-be-detected object 50 is present in the detection area 40; and under various environmental conditions (for example, the fan rotates, the curtain sways, and the like), the to-be-detected object 50 is not present in the detection area 40. Different from FIG. 17, FIG. 22 further includes step S360: determine, by using the machine learning model 64 according to the corrected signal, whether the to-be-detected object 50 is present in the detection area 40. If the to-be-detected object 50 is present, steps S370 and S390 continue to be performed to calculate information such as the distance information, the characterization information (such as movement information and physiological information) of the to-be-detected object 50; and if not, the process is ended. Through the machine learning technology, features about whether the to-be-detected object 50 is present can be learned, so as to determine whether the to-be-detected object 50 is present. In this way, in addition to saving operation resources when the to-be-detected object 50 is not present, erroneous determination can also be filtered (for example, a case that the characterization information is calculated when the to-be-detected object 50 is not present can be avoided).

Figures 23, 24:
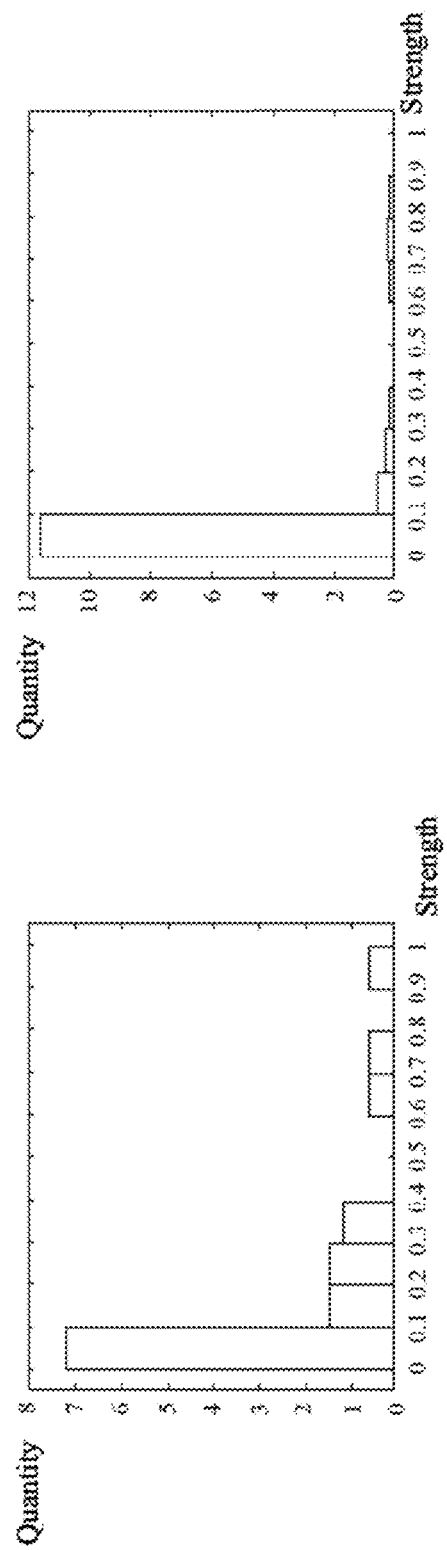
FIG. 23 is a histogram illustrating the to-be-detected object being not present.
FIG. 24 is a histogram illustrating the to-be-detected object being present.

In some embodiments, when the machine learning model 64 is to be trained and the machine learning model 64 is used for determination, feature extraction processing may be performed on the corrected signal in advance, and then an extracted feature is input to the machine learning model 64. The feature extraction processing may be statistics of a histogram and calculation of an average value, a standard deviation, a variance, skewness, kurtosis, and the like. The statistics of the histogram is given by way of example. Values of the two-dimensional array A2 of the corrected frequency domain signal SF' can be normalized, and a number of elements in each signal strength interval can be counted according to the normalized value. Referring to FIG. 23 and FIG. 24 together, histograms of the to-be-detected object 50 being not present and the to-be-detected object 50 being present are respectively illustrated. 10 signal strength intervals are given by way of example. It can be seen that the histograms in the two situations have different distributions.

Figure 25:
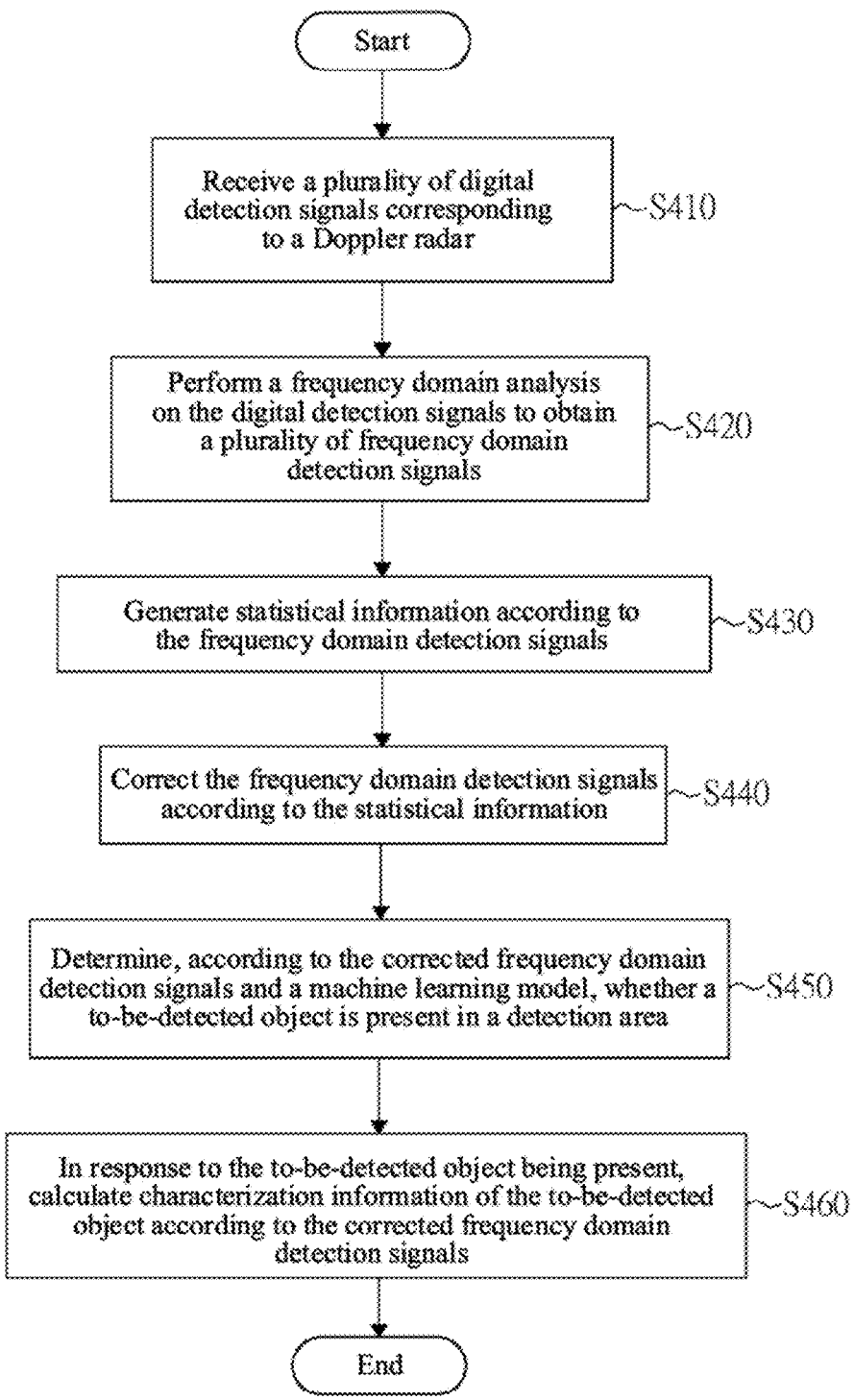
FIG. 25 is a flowchart of a characterization information detection method according to some embodiments.

FIG. 25 is a flowchart of a characterization information detection method according to some embodiments. The characterization information detection method may be performed by the processor 61 of the above signal processing device 60. In step S410, a plurality of digital detection signals (that is, the above digital signals SP) corresponding to the Doppler radar are received. In step S420, a frequency domain analysis is performed on the digital detection signals to obtain a plurality of frequency domain detection signals (that is, the above frequency domain signals SF). In step S430, statistical information (that is, the above statistical information SV) is generated according to the frequency domain detection signals. In step S440, the frequency domain detection signal is corrected according to the statistical information SV. Specifically, step S440 is to normalize the frequency domain detection signals according to the statistical information SV. The statistical information SV is an absolute sum of squares, an absolute maximum, a standard deviation, or a variance of the frequency domain detection signals in a statistical period. In step S450, it is determined, according to the corrected frequency domain detection signals (that is, the above corrected frequency domain signals SF') and the machine learning model 64, whether the to-be-detected object 50 is present in the detection area 40. In step 460, the characterization information of the to-be-detected object 50 is calculated according to the corrected frequency domain detection signals SF' in response to the to-be-detected object 50 being present. Relevant descriptions of the steps are described in detail above, and details are not described herein again.

In some embodiments, the machine learning model 64 is stored in an edge device or a cloud server, and the FMCW radar 10 transmits the extracted features to the edge device or the cloud server through the transmission module of the FMCW radar for subsequent machine model training or detection and determination. Alternatively, the FMCW radar 10 transmits the above corrected signals to the edge device or the cloud server through the transmission module of the FMCW radar for subsequent digital signal processing, machine model training, and/or detection and determination.

Based on the above, according to the FMCW radar and method for processing digital signals in some embodiments, the problem of poor signals caused by interference from static and dynamic environments can be solved, and an amount of to-be-processed data can be reduced to accelerate a processing speed. According to the FMCW radar and the method for processing digital signals in some embodiments, it can be identified whether the to-be-detected object 50 is present, so as to improve processing efficiency and filter erroneous determination.

What is claimed is:

1. A frequency modulated continuous wave (FMCW) radar, comprising:
    a transmitter configured to transmit a plurality of chirp signals; and
    a receiver configured to receive reflected chirp signals, generate a plurality of digital signals corresponding to the chirp signals, superpose the digital signals to obtain an output signal, and calculate a moving speed or a periodic-movement frequency of a to-be-detected object by performing Doppler Fourier transform according to the output signal so as to obtain movement information or physiological information of the to-be-detected object;
    wherein the receiver is further configured to:
        performing a Distance Fourier transform on a plurality of the output signal to obtain a plurality of frequency domain detection signals;
        reshaping the plurality of frequency domain detection signals into a two-dimensional array, each row of the two-dimensional array includes one of the plurality of frequency domain detection signals;
        generating statistical information by calculating statistical values of each column of the two-dimensional array;
        normalizing the frequency domain detection signals according to the statistical information;
        determining, according to a machine learning model, whether the to-be-detected object is present; and
        performing the Doppler Fourier transform on the two-dimensional array to obtain the movement information or the physiological information of the to-be-detected object, when determining that the to-be-detected object is present.

2. The FMCW radar according to claim 1, wherein the receiver superposes the digital signals corresponding to the chirp signals in the same frame to obtain the output signal.

3. The FMCW radar according to claim 1, wherein the receiver superposes the digital signals corresponding to the chirp signals in a plurality of adjacent frames to obtain the output signal.

4. The FMCW radar according to claim 3, wherein the receiver aligns the digital signals before superposing the digital signals.

5. The FMCW radar according to claim 1, wherein the transmitter comprises at least one transmitting antenna, and the receiver superposes the digital signals corresponding to the chirp signals from the same transmitting antenna.

6. The FMCW radar according to claim 5, wherein the receiver comprises a plurality of receiving antennas, and the receiver superposes the digital signals corresponding to the chirp signals received by one of the receiving antennas from the same transmitting antenna to obtain the output signal.

7. The FMCW radar according to claim 5, wherein the receiver comprises a plurality of receiving antennas, and the receiver superposes the digital signals corresponding to the chirp signals received by the receiving antennas from the same transmitting antenna to obtain the output signal.

8. The FMCW radar according to claim 1, wherein the transmitter comprises a plurality of transmitting antennas, and the receiver superposes the digital signals corresponding to the chirp signals from at least two of the transmitting antennas.

9. The FMCW radar according to claim 8, wherein the receiver comprises a plurality of receiving antennas, and the receiver superposes the digital signals corresponding to the chirp signals received by one of the receiving antennas from at least two of the transmitting antennas to obtain the output signal.

10. The FMCW radar according to claim 8, wherein the receiver comprises a plurality of receiving antennas, and the receiver superposes the digital signals corresponding to the chirp signals received by the receiving antennas from at least two of the transmitting antennas to obtain the output signal.

11. The FMCW radar according to claim 1, wherein the receiver further generates statistical information according to the output signal and normalizes the output signal according to the statistical information.

12. The FMCW radar according to claim 11, wherein the statistical information is an absolute sum of squares, an absolute maximum, a standard deviation, or a variance.

13. The FMCW radar according to claim 11, wherein the receiver determines, according to the normalized output signal and the machine learning model, whether the to-be-detected object is present in a detection area.

14. The FMCW radar according to claim 13, wherein when determining that the to-be-detected object is present, the receiver calculates the moving speed or the periodic-movement frequency of the to-be-detected object by performing Doppler Fourier transform according to the normalized output signal so as to obtain movement information or physiological information of the to-be-detected object.

15. A method for processing digital signals, performed by a processor in a signal processing device and comprising:
    superposing a plurality of digital signals corresponding to a plurality of chirp signals received by a receiving terminal of a Doppler radar to obtain an output signal; and
    calculating a moving speed or a periodic-movement frequency of a to-be-detected object by performing Doppler Fourier transform according to the output signal so as to obtain movement information or physiological information of the to-be-detected object;
    wherein the step of calculating a moving speed or a periodic-movement frequency of a to-be-detected object further comprising:

performing a Distance Fourier transform on a plurality of the output signal to obtain a plurality of frequency domain detection signals;

reshaping the plurality of frequency domain detection signals into a two-dimensional array, each row of the two-dimensional array includes one of the plurality of frequency domain detection signals;

generating statistical information by calculating statistical values of each column of the two-dimensional array;

normalizing the frequency domain detection signals according to the statistical information;

determining, according to a machine learning model, that the to-be-detected object is present; and in response to the to-be-detected object being present, performing the Doppler Fourier transform on the two-dimensional array to obtain the movement information or the physiological information of the to-be-detected object.

16. The method for processing digital signals according to claim 15, wherein the digital signals corresponding to the superposed chirp signals are located in the same frame or in a plurality of adjacent frames.

17. The method for processing digital signals according to claim 15, wherein before the step of superposing the digital signals corresponding to the chirp signals received by the receiving terminal of the Doppler radar to obtain the output signal, the method further comprises:

aligning the to-be-superposed digital signals.

18. The method for processing digital signals according to claim 15, further comprising:

generating statistical information according to the output signal; and normalizing the output signal according to the statistical information.

19. The method for processing digital signals according to claim 15, further comprising:

determining, according to the output signal and the machine learning model, whether the to-be-detected object is present in a detection area.

20. The method for processing digital signals according to claim 18, further comprising:

determining, according to the normalized output signal and the machine learning model, whether the to-be-detected object is present in a detection area.

21. The method for processing digital signals according to claim 20, wherein the step of calculating the moving speed or the periodic-movement frequency of the to-be-detected object by performing Doppler Fourier transform according to the normalized output signal is performed when it is determined that the to-be-detected object is present.

22. A characterization information detection method, comprising:

receiving a plurality of digital detection signals corresponding to a Doppler radar;

performing a frequency domain analysis on the digital detection signals to obtain a plurality of frequency domain detection signals;

reshaping the plurality of frequency domain detection signals into a two-dimensional array, each row of the two-dimensional array includes one of the plurality of frequency domain detection signals;

generating statistical information by calculating statistical values of each column of the two-dimensional array;

normalizing the frequency domain detection signals according to the statistical information;

determining, according to the normalized frequency domain detection signals and a machine learning model, that a to-be-detected object is present in a detection area; and in response to the to-be-detected object being present, calculating a moving speed or a periodic-movement frequency of the to-be-detected object by performing Doppler Fourier transform according to the normalized frequency domain detection signals to obtain movement information or physiological information of the to-be-detected object.

23. The characterization information detection method according to claim 22, wherein the statistical information is an absolute sum of squares, an absolute maximum, a standard deviation, or a variance of the frequency domain detection signals in a statistical period.

* * * * *